US009175309B2

(12) United States Patent
Yun et al.

(10) Patent No.: US 9,175,309 B2
(45) Date of Patent: Nov. 3, 2015

(54) RECOMBINANT ADENOVIRUS WITH ENHANCED THERAPEUTIC EFFECT AND PHARMACEUTICAL COMPOSITION COMPRISING SAID RECOMBINANT ADENOVIRUS

(75) Inventors: Chae-ok Yun, Seoul (KR); Joo-Hang Kim, Seoul (KR)

(73) Assignee: Industry-University Cooperation Foundation Hanyang University (KR)

( * ) Notice: Subject to any disclaimer, the term of this patent is extended or adjusted under 35 U.S.C. 154(b) by 692 days.

(21) Appl. No.: 10/491,313

(22) PCT Filed: Sep. 28, 2002

(86) PCT No.: PCT/KR02/01831
§ 371 (c)(1),
(2), (4) Date: Mar. 29, 2004

(87) PCT Pub. No.: WO03/029448
PCT Pub. Date: Apr. 10, 2003

(65) Prior Publication Data
US 2005/0002965 A1   Jan. 6, 2005

(30) Foreign Application Priority Data

Sep. 29, 2001   (KR) .............................. 2001-0061025

(51) Int. Cl.
*C12N 15/86*   (2006.01)
*A61K 48/00*   (2006.01)

(52) U.S. Cl.
CPC ............... *C12N 15/86* (2013.01); *A61K 48/00* (2013.01); *C12N 2710/10343* (2013.01); *C12N 2710/10345* (2013.01)

(58) Field of Classification Search
CPC ..................... C12N 15/86; C12N 7/00; C12N 2710/10332; C12N 2799/022; C12N 2710/10345
See application file for complete search history.

(56) References Cited

U.S. PATENT DOCUMENTS

| | | | | |
|---|---|---|---|---|
| 5,770,442 A | * | 6/1998 | Wickham et al. | 435/320.1 |
| 6,080,578 A | * | 6/2000 | Bischoff et al. | 435/325 |
| 6,136,594 A | | 10/2000 | Dalemans et al. | |
| 6,284,223 B1 | * | 9/2001 | Luiken | 424/9.6 |
| 6,312,699 B1 | * | 11/2001 | Curiel et al. | 424/233.1 |

FOREIGN PATENT DOCUMENTS

| | | |
|---|---|---|
| GB | WO96/31602 | 10/1996 |
| WO | WO94/29440 | 12/1994 |
| WO | WO 98/10084 | 3/1998 |
| WO | WO99/39734 | 8/1999 |
| WO | WO 00/65034 | 11/2000 |
| WO | WO 00/73424 A1 | 12/2000 |

OTHER PUBLICATIONS

Rogers et al (1997) Gene Therapy. 4: 1387-1392.*
Hall et al (1998) Biochimica et Biophysica Acta. 1415: 101-113.*
Stone et al (2000) J of Endocrinology. 164: 103-118.*
Herrmann and Mathews (1989) Molecular and Cellular Biology. 9(12): 5412-5423.*
Ginsberg et al (1999) PNAS. 96: 10409-10411.*
Freund et al (1993) FEBS. 320(2): 97-100.*
Thoma et al (2000) Gene Therapy. 7: 1039-1045.*
Hopkins (1993) PNAS. 90: 8759-8760.*
Belousova et al. J Virol. Sep. 2002; 76(17): 8621-8631. Modulation of Adenovirus Vector Tropism via Incorporation of Polypeptide Ligands into the Fiber Protein.*
Dmitriev, Igor et al., "An Adenovirus Vector with Genetically Modified Fibers Demonstrates Expanded Tropism via Utilization of a Coxsackievirus and Adenovirus Receptor-Independent Cell Entry Mechanism", Journal of Virology, The American Society for Microbiology, vol. 72, No. 12, Dec. 1998, pp. 9706-9713.
Hall, Michael P. et al., "Interactions of a vesicular stomatitis virus G protein fragment with phosphatidylserine: NMR and fluorescence studies", Biochimica et Biophysica Acta, vol. 1415, No. 1. Dec. 9, 2008, pp. 101-113.
Lee, Heuiran et al., "Oncolytic Potential of E1B 55 kDa-Deleted YKL-1 Recombinant Adenovirus: Correlation with p53 Functional Status" International Journal of Cancer, vol. 88, No. 3, Nov. 1, 2000, pp. 454-463.
Kirby, Ian et al., "Identification of Contact Residues and Definition of the CAR-Binding Site of Adenovirus Type 5 Fiber Protein", Journal of Virology, The American Society for Microbiology, US, vol. 74, No. 6, Mar. 2000, pp. 2804-2813.
Caplen, N.J. et al., "Adeno-retroviral chimeric viruses as in vivo transducing agents", Gene Therapy, vol. 6, No. 3, Mar. 1999, pp. 454-459.
Yoshida, Yoko et al., "Highly Efficient VSVG-Pseudotyped Retroviral Packaging System Through Adenovirus-Mediated Inducible Gene Transduction", Cancer Gene Therapy, vol. 3, No. 6, p. S-21.
Liu, Miao-Liang et al., "Pseudotransduction of Hepatocytes by Using Concentrated Pseudotyped Vesicular Stomatitis Virus G Glycoprotein (VSV-G)-Moloney Murine Leukemia Virus-Derived Retrovirus Vectors: Comparison of VSV-G and Amphotropic Vectors for Hepatic Gene Transfer", Journal of Virology, The American Society for Microbiology, vol. 70, No. 4, Apr. 1996, pp. 2497-2502.
Arai, Tohru et al., "A New System for Stringent, High-Titer Vesicular Stomatitis Virus G Protein-Pseudotyped Retrovirus Vector Induction by Introduction of Cre Recombinase into Stable Prepackaging Cell Lines", Journal of Virology, The American Society for Microbiology, vol. 72, No. 2, Feb. 1998, pp. 1115-1121.
Yun, Cheo-Ok et al., "dl-VSVG-LacZ, a Vesicular Stomatitis Virus Glycoprotein Epitope-Incorporated Adenovirus, Exhibits Marked Enhancement in Gene Transduction Efficiency", Human Gene Therapy, vol. 14, No. 17, Nov. 20, 2003, pp. 1643-1652.
Dmitriev, Igor, et al., "An Adenovirus Vector with Genetically Modified Fibers demonstrates Expanded Tropism via Utilization of a Coxsackievirus and Adenovirus Receptor-Independent Cell Entry Mechanism," *J. Virology*, 72(12): 9706-9713 (1998).

(Continued)

*Primary Examiner* — Michelle S Horning
(74) *Attorney, Agent, or Firm* — Swanson & Bratschum, L.L.C.

(57) ABSTRACT

Disclosed is a recombinant adenovirus with a protein containing a VSV-G epitope derived from vesicular stomatitis virus (VSV). Also, the present invention discloses a pharmaceutical composition comprising such a recombinant adenovirus and a pharmaceutically acceptable carrier. Further, the present invention discloses a recombinant plasmid capable of expressing the recombinant adenovirus and a host cell transformed with the recombinant adenovirus.

4 Claims, 42 Drawing Sheets

(56) References Cited

OTHER PUBLICATIONS

Feng, Meizhen, et al., "Stable in vivo gene transduction via a novel adenoviral/retroviral chimeric vector," *Nature Biotechnology*, 15:866-870 (1997).

Heise, Carla, et al., "ONYX-015, and E1B gene-attenuated adenovirus, causes tumor-specific cytolysis and antitumoral efficacy that can be augmented by standard chemotherapeutic agents," *Nature Medicine*, 3(6): 639-645 (1997).

Raikwar, Sudhanshu P., et al., "Recombinant adenovirus synthesizing cell surface-anchored βhCG induces bioneutralizing antibodies in rats," *Gene*, 190: 197-202 (1997).

Shinoura, Nobusada, et al., "Highly Augmented Cytopathic Effect of a Fiber-mutant E1B-defective Adenovirus for Gene Therapy of Gliomas," *Cancer Research*, 59: 3411-3416 (1999).

Tomko, Richard P., et al., "HCAR and MCAR: The human and mouse cellular receptors for subgroup C adenoviruses and group B coxsackieviruses," *Proc. Natl. Acad. Sci. USA*, 94: 3352-3356 (1997).

Yoshida, Yoko, et al., VSV-G-Pseudotyped Retroviral Packaging through Adenovirus-Mediated Inducible Gene Expression, *Biochem. and Biophys. Res. Comm.*, 232(2):379-382 (1997).

Van Geer et al., "Ephrin A2 receptor targeting does not increase adenoviral pancreatic cancer transduction in vivo" World J. Gastroenterology, Jun. 14, 2009, 15(22) 2754-2762, 2009, The WJG Press and Baishideng.

Schoggins et al., "Serotype 5 Adenovirus fiber (F7F41S) chimeric vectors incur packaging deficiencies when targeting peptides are inserted into Ad41 short fiber" Virology, Dec. 5, 2009; 395(1): 10-20, 2009, J. Virol.

Matsui et al., "Development of fiber-substituted adenovirus vectors containing foreign peptides in the adenovirus serotype 35 fiber knob" Gene Therapy, 2009, 16: 1050-1057, 2009 Macmillan Publishers.

Wickham et al. (1997) Journal of Virology 71(11):8221-8229 "Increased In Vitro and In Vivo Gene Transfer by Adenovirus Vectors Containing Chimeric Fiber Proteins."

Office Action dated Nov. 20, 2006 issued in Japanese patent application 2003-532665.

Lee, H, et al., Efficient gene transfer of VSV-G pseudotyped retroviral vector to human brain tumor, Gene Therapy, Feb. 2001, vol. 8, p. 268-273.

Lee, H., et al., Oncolytic potential of E1B 55 kDa-Deleted YKL-1 recombinant adenovirus: correlation with p53 functional status, Int J Cancer, 2000, vol. 88, p. 454-463.

Yoshikda, Yoko, et al., VSV-G-Pseuodtyped retroviral packaging through adenovirus-mediated inducible gene expression, Biochemical and Biophysical Research Communications, 1997, vol. 232, p. 379-382.

Sinnis et al. (1994) "Structural and Functional Properties of Region II-Plus of the Malaria Circumsporozoite Protein" J. Exp. Med., V. 180: 297-306.

Hong et al. (1996) "Domains Required for Assembly of Adenovirus Type 2 Fiber Trimers" J. Virology, V. 70(10): 7071-7078.

Desgrosellier et al. (2010) "Integrins in Cancer: Biological Implications and Therapeutic Opportunities", V. 10: 9-23.

Coughlan et al. (2010) "Tropism-Modification Strategies for Targeted Gene Delivery Using Adenoviral Vectors" Viruses, V. 2: 2290-2355.

Sanderson et al. (2004) "Heparan Sulfate Proteoglycans and Heparanase—Partners in Osteolytic Tumor Growth and Metastasis", Matrix Biology, V. 23: 341-352.

\* cited by examiner

FIG. 1

Lec 2

RECOMBINANT ADENOVIRUS WITH ENHANCED THERAPEUTIC EFFECT AND PHARMACEUTICAL COMPOSITION COMPRISING SAID RECOMBINANT ADENOVIRUS

RELATED APPLICATIONS

This application is the U.S. National Stage of International Application No. PCT/KR02/01831, filed 28 Sep. 2002, published in English, which application claims priority under 35 U.S.C. §119 or 365 to Korea Application No. 2001-0061025, filed 29 Sep. 2001.

TECHNICAL FIELD

The present invention relates, in general, to a recombinant adenovirus with improved therapeutic efficacy, and more particularly, to a recombinant adenovirus prepared by introducing a ligand responsible for infection of vesicular stomatitis virus (VSV) into adenovirus. Also, the present invention is concerned with a pharmaceutical composition comprising such a recombinant adenovirus.

BACKGROUND ART

With recent rapid developments in molecular biology, considerable advance has been made in development of therapeutic agents for various cancers and other intractable diseases using recombinant DNA technologies. Also, since gene therapy was first attempted clinically in 1990, studies on delivery systems of therapeutic genetic materials have been carried out. Among clinical gene therapies, about 60% focus on treating cancers, and various vectors based on human or non-human viruses have been developed as vehicles to transfer therapeutic genes into target cells, in which adenovirus with many advantages as a gene transfer vehicle is attractive as a substitute for retroviruses.

For practical use of gene therapy in clinical fields, first of all, gene transfer vehicles capable of safely and effectively delivering therapeutic genes to targeted regions should be developed. The potential of recombinant adenovirus as a gene transfer vehicle was reported in 1984 by Graham, F. L. (Graham, F. L., EMBO J., 1:2917-2922, 1984). Since the first clinical trial of gene therapy in adenosine deaminase (ADA)-deficient patients in 1990, active research into gene therapy was performed until the mid-1990s, in which expression of a specific gene was induced in target cells using replication-defective recombinant adenoviral vectors constructed by inserting the specific gene thereinto. Such research was promoted by the fact that adenovirus has many benefits as a gene transfer vehicle, in terms of being excellent in transferring exogenous genes into a variety of cell types regardless of cell cycle state of target cells, easily producing high-titer virus, being capable of being lyophilized and thus structurally stable, and being easily formulated into pharmaceutical preparations (Yeh, P. et al., FASEB J., 11:615-622, 1997).

However, adenovirus has several significant problems in mediating gene transfer, including the relatively short-term expression of foreign genes and the induction of strong immune response to viral proteins and virus-infected cells. To overcome such problems, various efforts to modify structure of adenovirus have been made. For example, it was reported by S. Kochaneck in 1996 that gutless virus produced by removing all adenoviral coding sequences is advantageous in terms of being capable of carrying maximum 30 kb of foreign genes, as well as not producing viral proteins and thus not inducing immune response in host cells (Kochanek, S., Proc. Natl. Acad. Sci. 93:5731-5736, 1996). Korean Pat. Publication No. 1999-22941 discloses an adenovirus vector having no overlap with a suitable packaging cell line, in which adenovirus loses self-replication ability and is incapable of being encapsidated, thus avoiding interference with the host immune system.

Since recombinant adenovirus was known to be effective in gene therapy and easily delivered into a body owing to being produced in high titer and easily concentrated, clinical cancer gene therapy mediated by recombinant adenovirus has rapidly increased in the past five years. When cancer is treated using gene therapy mediated by recombinant adenovirus, since prolonged and continuous expression of therapeutic genes is not required, and host immune response induced by virus or viral proteins is not essential and can be advantageous in some cases, adenovirus become attractive as a gene transfer vehicle for cancer therapy (Pallard, F. Hum. Gene Ther., 9:283-286, 1998).

Most recombinant adenoviruses for cancer therapy, which carry a single therapeutic gene, are gene transfer systems first used in cancer gene therapy. Recently, efforts have been made to improve therapeutic efficacy of gene therapy through simultaneous expression of two therapeutic genes encoding proteins with different functions, rather than expression of one gene, or adenovirus-mediated gene therapy in combination with administration of antitumuor agents or radiotherapy, which have been commonly used for cancer therapy (Roth, J. A. et al., J. Nat. Cancer Ins., 89:21-39, 1997). For example, Korean Pat. No. 1997-5206 discloses a method of treating cancer using recombinant adenovirus harboring the p53 gene, known to have an antitumor effect, in which the recombinant adenovirus does not produce replication-competent viral particles and thus displays effective antitumor activity.

However, it has been reported that such replication-incompetent adenoviral vectors can induce antitumor activity in only primary infected cells or a very small number of surrounding cells. Therefore, a great number of recombinant adenovirus should be administered at once or administered repeatedly over several times, thus inducing cellular immunity and limiting its clinical applications. To overcome such problems, a variety of efforts have been made to develop a modified adenovirus capable of selectively replicating in and killing tumor cells, since the McCormick research group reported a recombinant adenovirus. The E1B 55 kDa gene-deleted adenovirus ONYX-015 (dl1520), which was developed by McCormick, selectively replicates and induces cytolysis in tumor cells lacking functional $p53^3$ (Heise, C. et al., Nature Med., 3:639-645, 1997). In clinical trials for the treatment of head and neck cancer, the recombinant adenovirus ONYX-015 showed excellent therapeutic efficacy. Furthermore, another type recombinant adenovirus prepared by inserting a cancer-specific gene-regulatory region into E1 region was developed, in which viral proliferation is induced in a cancer tissue-specific manner. Also, antitumor effect and safety of a recombinant adenoviral vector can be improved by inserting the herpes simplex virus-thymidine kinase (HSV-TK) gene or CD gene into the E1 region, and thus the recombinant adenovirus loses its proliferation capacity (Freytag et al., Nat. Biotech., 15:866-870, 1997). In this regard, adenovirus-mediated gene therapy can be clinically applied under various circumstances. In particular, the recombinant adenovirus with tumor cell-specific cytotoxic effect was demonstrated to be more effective in cancers associated with mutations in the p53 gene, such as brain cancer, which is resistant to previous chemotherapies or radiation therapies (Shinoura, N. et al., Cancer Res. 59:3411-3416, 1999). However, administration of a high titer of adenovirus to brain is limited by its toxicity. Thus, methods of enhancing gene delivery efficiency should be developed in order to reduce the administration amount of adenovirus.

Adenovirus infects host cells mainly through coxsackievirus and adenovirus receptor (CAR) on the host cells (Tomko, R. P. et al., Proc. Natl. Sci. USA 94:3352-3356, 1997). Most cells in the host typically express sufficient amount of CAR, but no or little expression of CAR is found in muscle cells in matured bone tissues, lymphocytes, fibrocytes, pulmonary macrophages and some tumor cells, where adenovirus-mediated gene transfer efficiency is relatively low. Recent clinical trials using adenovirus as a gene delivery vehicle demonstrated that poor gene delivery into several tumor cells is attributed to lack of expressed CAR on the tumor cells. In addition, the recombinant adenovirus can infect normal cells with relatively high expression of CAR rather than target cells (tumor cells) with a low CAR level, resulting in reduction of its infection rate into tumor cells. To overcome such low transduction efficiency and lack of specificity for target cells by the recombinant adenovirus, there is a need for development of high-titer adenovirus. However, the high-titer adenoviral vectors can have increased toxicity and induce immune response in the host, thus threatening safe and effective clinical cancer therapy.

The disadvantages of recombinant adenoviral vectors in gene therapy owing to the above reasons can be overcome through infection of adenovirus into target cells in a CAR-independent manner. Effective gene transfer on epithermal cell was found when adenovirus type 2 fiber protein is replaced with that of adenovirus type 17. Also, a chimeric adenovirus prepared by replacing the knob domain of adenovirus type 5 with the knob domain of adenovirus subgroup B was demonstrated to effectively infect bone marrow cells not easily infected with adenovirus type 5. Wickham, T. J. J. reported that introduction of a polylysine motif or Arg-Gly-Asp (RGD)-containing peptide motif at the C-terminal region of adenovirus fiber protein allows adenovirus to specifically recognize alternative receptors, cell surface receptors including heparin and the integrin receptor, leading to successful infection of the virus (Wickham, T. J. J. Virol., 71:8221-8229, 1997). In addition, Kransnykh, V. et al., reported that transduction efficiency of adenovirus can be increased by inserting a targeting group capable of recognizing and then binding a target cell-specific receptor into the HI loop of the adenovirus fiber (Kransnykh, V. et al., J. Viro., 72:1884-1852, 1998; Yoshida, Y. et al., Hum. Gene. Ther. 9:2503-2515, 1998; and Shinoura, N. et al., Cancer Res. 59:3411-3416, 1999). However, such modifications were not sufficient for improvement of the transduction efficiency of adenovirus, and there are still efforts to develop a method of increasing the trasduction efficiency of adenovirus.

A plurality of patents and papers are referred and cited herein. All references cited herein are incorporated herein by reference in their entireties, and the current state of the conventional techniques in the art and the features of the present invention will be more clearly understood with the cited references.

DISCLOSURE OF THE INVENTION

Leading to the present invention, the intensive and thorough research into recombinant adenovirus with improved therapeutic efficacy, conducted by the present inventors, resulted in the finding that a recombinant adenovirus comprising a protein containing a VSV-G epitope, which is prepared by introducing the protein into an adenovirus, has improved transduction efficiency and thus enhanced therapeutic effect in adenovirus-based gene therapy, especially increasing tumor cell-killing effect of adenovirus, which is achieved in a CAR-independent manner.

It is, therefore, an object of the present invention provides a recombinant adenovirus with improved therapeutic efficacy for various diseases, including improved tumor cell-killing effect.

It is another object of the present invention provides a pharmaceutical composition comprising the recombinant adenovirus.

In an aspect of the present invention, there is provided a recombinant adenovirus comprising a protein containing a VSV-G epitope derived from vesicular stomatitis virus, which has improved therapeutic efficacy.

In another aspect of the present invention, there is provided a pharmaceutical composition comprising: (a) a therapeutically effective amount of a recombinant adenovirus comprising a protein containing a VSV-G epitope derived from vesicular stomatitis virus; and (b) a pharmaceutically acceptable carrier.

BRIEF DESCRIPTION OF THE DRAWINGS

The above and other objects, features and other advantages of the present invention will be more clearly understood from the following detailed description taken in conjunction with the accompanying drawings, in which:

Figure 1:
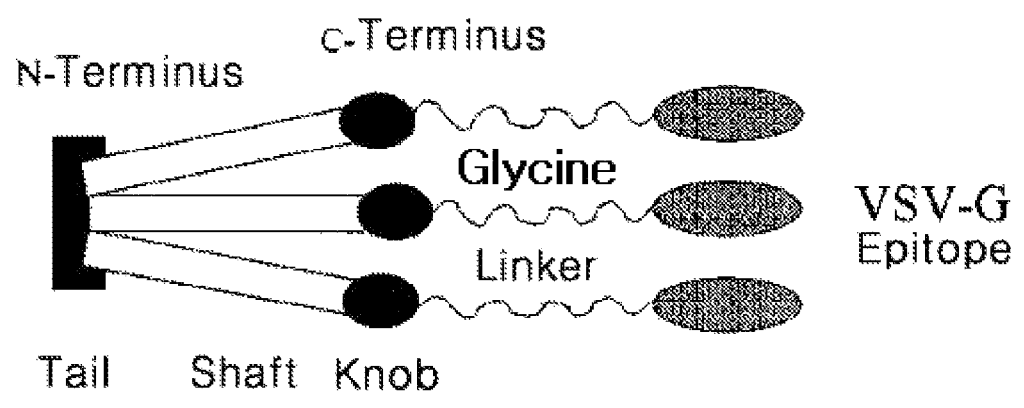

FIG. 1 is a schematic representation of the C-terminus of adenovirus fiber protein to which the VSV-G epitope is attached through a glycine linker;

BEST MODES FOR CARRYING OUT THE INVENTION

Figure 2:
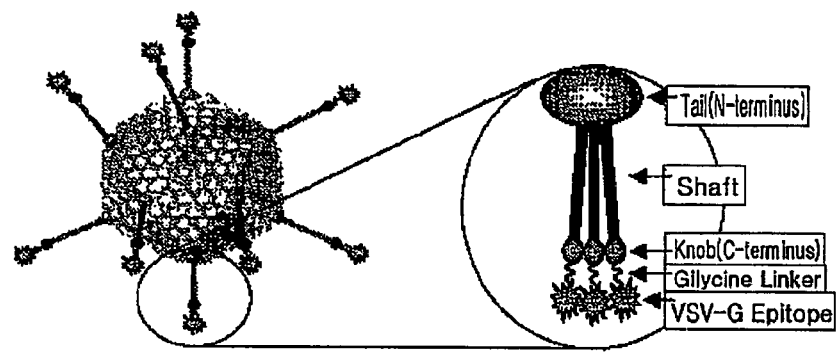
FIG. 2 is a schematic representation of a retargeting infection pathway of a recombinant adenovirus YCI-Ad-VSVG of the present invention carrying a VSV-G epitope into a target cell.
Figure 2:
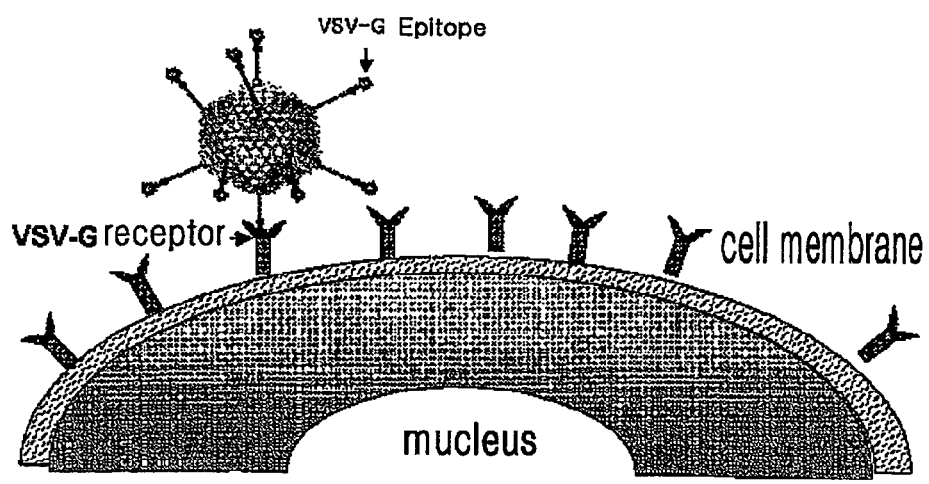
Figure 3:
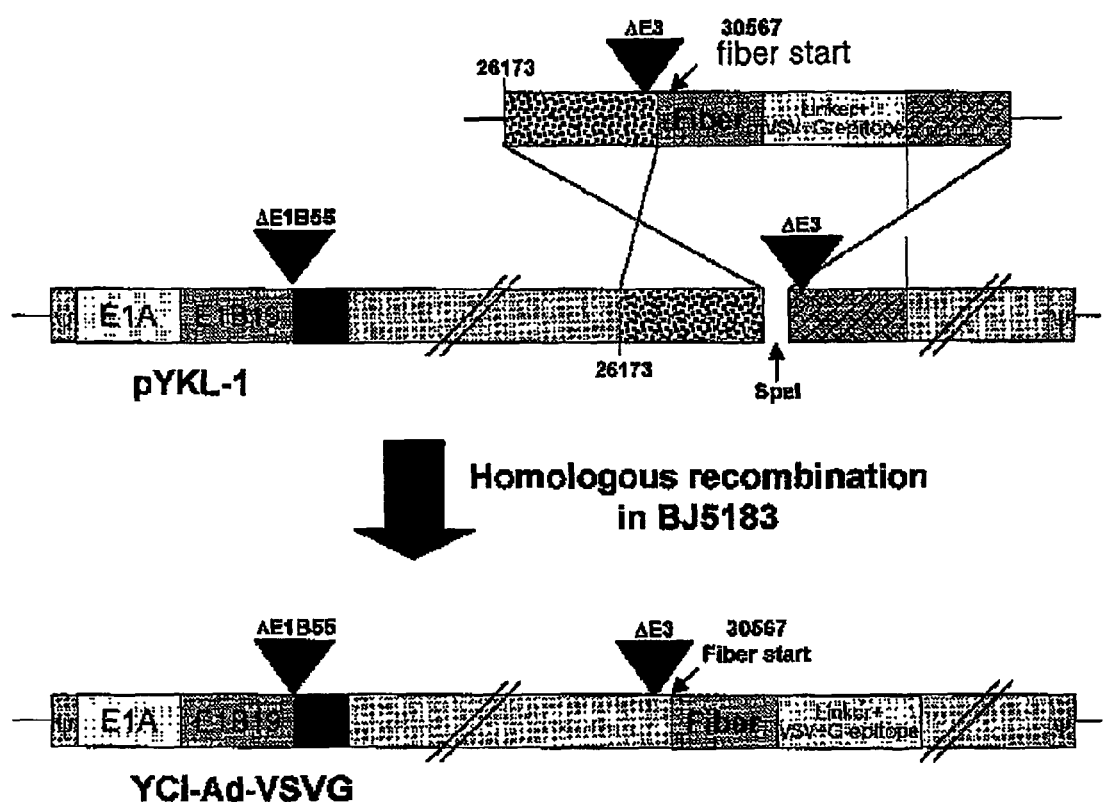
FIG. 3 shows a schematic representation of the construction of the recombinant adenovirus YCI-Ad-VSVG carrying a VSV-G epitope gene and a process for preparing the recombinant adenovirus through homologous recombination.
Figure 4:
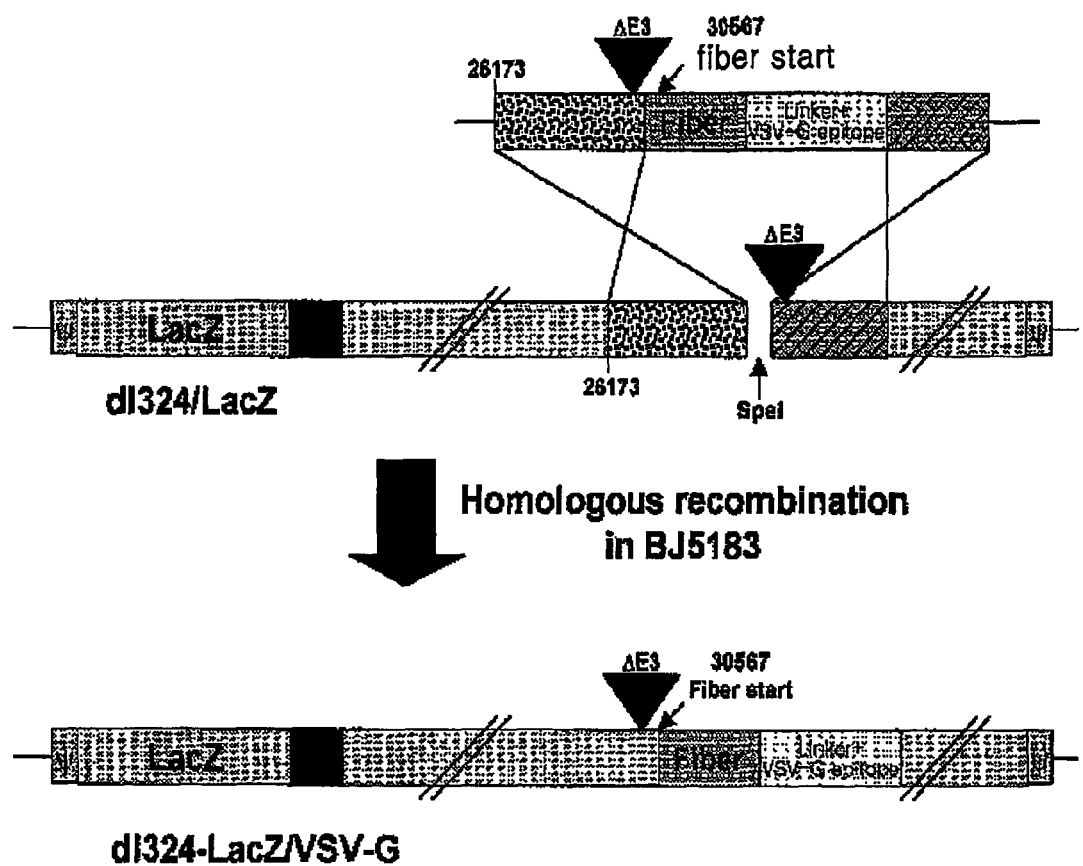
FIG. 4 shows a schematic representation of the construction of the recombinant adenovirus dl324-LacZ-VSVG with a VSV-G ligand incorporated into the carboxy terminus of the fiber protein and a process for preparing the recombinant adenovirus through homologous recombination.

The present invention is directed to a recombinant adenovirus comprising a protein containing an epitope derived from vesicular stomatitis virus G-protein (VSV-G), which is prepared by introducing the protein into adenovirus.

Adenovirus useful in the present invention includes adenovirus type 1, type 2, type 3, type 4 and type 5, and most preferably, type 5. In addition, all types of adenovirus used in the present invention may be replication-competent or replication-incompetent. E1A gene is known to be essential for replication of adenovirus. Thus, replication-competent adenovirus constructed in the present invention contains an E1A gene, and replication-incompetent adenovirus constructed in the present invention is E1A-deleted or carries a mutated E1A gene. In accordance with the present invention, a replication-competent recombinant adenovirus comprising a protein containing a VSV-G epitope infects tumor cells at high efficiency in a CAR-independent manner, replicates in the tumor cells and then eventually kills the tumor cells wiht high efficiency. On the other hand, a replication-incompetent recombinant adenovirus comprising a protein containing a VSV-G epitope according to the present invention, which typically carries one or more therapeutic genes, entries into target cells via CAR-independent infection at high efficiency, and expresses the therapeutic genes in the target cells, thus allowing treatment of various diseases including cancer, with improved therapeutic efficacy.

Mutation at the tumor suppressor gene p53 is found in about 50% of human cancers including non-small cell lung cancer, large intestine cancer, breast cancer, head and neck cancer and ovarian cancer (Brennan J. A. et al., N. Engl. J. Med., 332, 429-435, 1995; Bergh et al., Nature Med., 1, 1029-1034, 1995; and Perkins, A S. and Steern, D. F., Lippincott-Raven, 5th edition, Philadelphia, 79-102, 1997). In addition, in many cancer patients harboring the wild-type p53 protein, p53 was demonstrated to be inactivated by overexpression of mdm2 gene (Leach F. S. et al., Cancer Res., 53, 2231-2234, 1993; and Marchetti A. et al., Dign. mol. Pathol., 4, 93-97, 1995), infection with human papilloma virus (Scheffner M. et al., Cell., 63, 1129-1136, 1990; and Joseph, R. N. and Vogt, P. K., Lippincott-Raven, 3rd edition, New York, 301-343, 1996), or other unknown mechanisms (Chang, F., et al., J. Clin. Oncol., 13, 1009-1022, 1995). The functional loss of p53 is associated with the pathogenic states at the terminal stages of human cancers, for example, unfavorable convalescence and resistance after typical cancer therapy (Harris, C. C. and Holstein, M., N. Engl. J. Med., 10 329, 1318-1327, 1993; and Kirsch, D. G. and Kastan, M. B., J. Clin. Oncol., 16, 3158-3168, 1998). E1 gene, which is one of the adenovirus early genes, is an essential factor for replication of adenovirus, and encodes a plurality of open reading frames, including those for E1A, E1B-19 kDa and E1B-55 kDa (Graham F. L. et al., J. Gen. Virol., 36, 59-72, 1987; and Shenk, T. Lippincott-Raven, 3rd edition, 2111-2148, New York, 1996). The E1A protein, which is a transcriptional factor binding to pRB, p300 and other transcription regulatory proteins, mainly functions to convert the adenovirus-infected cells to S phase, at which the viral genome is replicated (Shenk, T. Lippincott-Raven, 3rd edition, 2111-2148, New York, 1996; and Shenk, T. and Flint, S. J., Adv. Cancer Res., 57, 47-85, 1991). The E1A expression and unpredicted synthesis of exogenous DNA induce the expression and activation of p53 known as a tumor suppressor gene (Lowe, S. W. and Ruley, H. E., Genes Develop., 7, 535-545, 1993; and Nakajima T. et al., JBC., 273, 20036-20045, 1998). In contrast, the E1B-55 kDa protein physically binds to and inactivates the p53 protein (Yew, P. R. and Berk, A. J., Nature, 357, 82-85, 1992; and Joseph, R. N. and Vogt, P. K., Lippincott-Raven, 3rd edition, New York, 301-343, 1996). Therefore, using such a functional mechanism of the E1B-55 kDa protein, wild-type adenovirus can be modified for effective replication and proliferation in host cells through control of the host cells. Since the binding of the E1B-55 kDa protein encoded by an adenovirus E1B gene to p53 inhibits the function of p53, leading to induction of viral proliferation and eventually lysis of infected cells, adenovirus used in the present invention includes E1B-55 kDa-attenuated or deleted adenovirus. The E1B-55 kDa-attenuated recombinant adenovirus developed by Bischoff J. et al. was known to selectively replicate and induce cytolysis in p53-deficient cells including most human tumor cells (Bischoff J. et al., Science, 274, 373-376, 1996). Such E1B-55 kDa-attenuated recombinant adenovirus is known to serve as an effective oncolytic agent in in vitro and in vivo tests (Heise C. et al., Nature Med., 3, 639-645, 1997), and encouraging data was also obtained in its clinical trials for the treatment of recurrent head and neck cancer (Kim D. et al., Nature Med., 4, 1341-1342, 1998). The present inventors reported that the YKL-1 adenovirus with a mutated E1B-55 kDa gene selectively replicates in tumor cells with p53 mutations and kills the tumor cells (Lee H. et al., Int. J. Cancer 2000;88:454-463; and Kim J. S. et al., J. Korean Cancer Assoc 2000;32(l):200-209).

The E1B gene, expressed at the early phase of infection, encodes the E1B-19 kDa and E1B-55 kDa proteins. The E1B-19 kDa protein is encoded by a nucleotide sequence similar to that of Bcl-2 acting as a potential apoptosis suppressor, and has similar function to Bcl-2 (Chiou S. K. et al., J. Virol 1994;68(10):6553-6566). The E1B-19 kDa protein is known to inhibit apoptosis mediated by the adenovirus (Ad) E1A protein, as well as by p53 in tumor cells (Debbas M. et al., Genes Dev 1993, 7:546-554; and Han J. et al., Genes Dev 1996, 10:461-477). Also, the functional similarity between E1B-19 kDa and Bcl-2 is found in that both of them suppress apoptosis induced by removal of growth factor, radiotherapy or antitumor agents (Huang D. C., Oncogene 1997, 14:405-414). Therefore, E1B-19 kDa-deficient, replication-competent adenovirus may be also useful for gene therapy. The E1B19 gene-deleted recombinant adenovirus, constructed by the present inventors, was reported to have excellent tumor cell-killing effect and a spread oncolytic effect to surrounding tumor cells, by inducing apoptosis by viral proliferation in adenovirus-infected cells (Kim J. S. et al., Cancer Gene Therapy 2002, 9:725-736; and Kim J. S. et al., Cancer Research and Treatment 2001, 33(6):500-511).

In addition, adenovirus preferably used in the present invention includes E1B-55 kDa and E1B-19 kDa-deficient adenovirus.

In accordance with another aspect of the present invention, adenovirus useful in the present invention includes an E1/E3-deleted replication-incompetent adenovirus. Such an E1E3-deleted replication-incompetent adenovirus has been widely used in gene therapy because of having gene transfer efficiency relatively higher than other adenovirus vectors and expressing trans-genes in a broad spectrum of cell types. Therapeutic genes are typically introduced into adenovirus by replacing the E1A gene essential for viral replication. Various genes encoding proteins having antitumor activity and eventually degenerating tumor cells, including cytokine genes, immunostimulating factor genes, suicide genes and tumor suppressor genes can be introduced into the adenovirus. The suicide genes encode enzymes capable of conferring to tumor cells sensitivity to chemotherapeutic agents, or of inducing toxic conditions in tumor cells. The most well-known suicide gene is the herpes simplex virus-thymidine kinase (HSV-TK) gene (U.S. Pat. Nos. 5,631,236 and 5,601, 818). Cells expressing HSV-TK are susceptible to selective cell death by the nucleoside analog ganciclovir. The tumor suppressor genes encode polypeptides functioning to inhibit formation of tumor. The tumor suppressor genes are naturally occurring, and their deletion or inactivation is believed to be a prerequisite for the incidence of tumor.

Examples of the tumor suppressor genes include members of the tumor suppressor gene INK4 family, which are exemplified by APC, DPC4, NF-1, NF-2, MTS1, WT1, BRCA1, BRCA2, VHL, p53, p110Rb, p16 and p21, and therapeutically effective fragments thereof (e.g., p56Rb, p94Rb). It will be understood that other known antitumor genes can be used by those of ordinary skill in the art.

In addition, a variety of therapeutic genes useful in treating various diseases are known. Non-limiting examples of the therapeutic genes include genes encoding cytokines (e.g., interferon-α, interferon-β, interferon-δ and interferon-γ), interleukin (e.g., IL-1, IL-2, IL-4, IL-6, IL-7 and IL-10), and colony-stimulating factors (e.g., GM-CSF and G-CSF). Further, the therapeutic genes include genes encoding tissue-type plasminogen activator (tPA) or urokinase-type plasminogen activator (uPA) (Trends in Cardiovascular Medicine, Vol. 3, No. 2, 1993, p61), and the gene encoding lysosomal acid lipase (LAL) essential for the hydrolysis of cholesterol esters and triglycerides that are delivered to the lysosomes via the low density lipoprotein receptor system and thus preventing hyperlipidemia (Proceeding the National Academy of Science, Vol. 90, April 1993, p.2812). Also, nucleotides available for treatment of various diseases including cystic fibrosis, adenosine deaminase deficiency, AIDS and other infectious diseases, and malignant and inflammatory diseases are known to be useful as therapeutic genes, which are obtainable from DNA sequence databanks such as GenBank or EMBL.

The VSV-G epitope, which is a part of the envelope glycoprotein of vesicular stomatitis virus (VSV-G), is responsible for infection of VSV into a wide variety of host cells (Ory, D. S. et al., Proc. Natl. Sci. USA, 93:11400-11406, 1996). The VSV-G epitope binds to phosphatidyl serine overexpressed on cell membranes of a broad range of human cells. Therefore, the present invention is characterized by introducing a protein containing a VSV-G epitope, directly associated with binding to phosphatidyl serine on cell membranes of human cells, to an adenovirus. The protein containing a VSV-G epitope comprises an oligopeptide having an amino acid sequence given in SEQ ID NO 9, and includes a glycoprotein containing the oligopeptide and all derivatives from the glycoprotein.

In accordance with the present invention, the protein containing a VSV-G epitope is linked to any position of the adenovirus proteins, including the adenovirus fiber, capsid and penton base. It is known that an exogenous ligand can be introduced into the HI loop of the fiber knob, penton base or the carboxy terminus of the fiber of adenovirus (Kirby, I. et al., J. Virol., 74:2804-2813, 2000). The carboxy terminus of the fiber protein, which is present at the most distant position from the body of adenovirus, practically participates in binding of adenovirus to its primary receptor CAR. That is, the carboxy terminus of fiber protein is the most optimal site for recognition of and binding to phosphatidyl serine on cell membranes by adenovirus via the VSV-G epitope. Therefore, in accordance with the present invention, the protein containing a VSV-G epitope is linked to the knob of the adenovirus fiber protein, and more preferably, the carboxy terminus of the fiber. FIGS. 1 and 2 show an embodiment of linkage of a VSV-G epitope to the terminal end of the adenovirus fiber protein.

In a preferred aspect of the present invention, there is provided a recombinant adenovirus containing a VSV-G epitope derived from vesicular stomatitis virus linked to the carboxy terminus of the adenovirus fiber protein, which has improved oncolytic effect.

The introduction of the protein containing a VSV-G epitope into adenovirus may be achieved using conventional techniques known in the art. Various approaches to CAR-independent infection of adenovirus have been attempted, and such alternative infection can be achieved by both genetic and immunologic methods. The immunologic retargeting strategy is based on conjugates, in which adenovirus is conjugated with targeting molecules. Such a method requires a multi-component system. The genetic strategy includes modification of viral structures using genetic engineering techniques, which is relatively advantageous in terms of requiring only a single-component system.

As an example of the conjugate-based strategy to develop a targeted adenovirus infecting cells via an alternative pathway, the surface of adenoviral vectors is coated with bispecific retargeting conjugates. Such a method was introduced first in 1996 by the Douglas research group, in which folate was chemically conjugated to the neutralizing Fab fragment of an anti-knob monoclonal antibody, leading to alter the adenoviral native tropism and thus produce a recombinant adenovirus with a novel tropism. The bispecific retargeting conjugates allow tissue-specific retargeting of the virus and tumor-cell specific gene delivery.

In case of genetic targeting strategies, a targeted adenovirus may be developed by modification of the adenovirus fiber, penton base and hexon capsid proteins. Since the fiber knob is essential for binding of adenovirus to CAR, the targeting of adenovirus is mainly achieved by modification of the fiber protein. In order to genetically modify the fiber knob region binding to CAR to alter adenoviral tropism, the trimeric structure of the fiber should be preserved, and a targeting ligand should be well expressed in a form of being conjugated with the fiber, and thus bind accurately to a specific receptor for the targeting ligand. To express a targeting ligand conjugated to the fiber on the surface of adenovirus, the transcriptional stop codon is deleted from the fiber protein and a gene encoding the targeting ligand is inserted to the stop site, thus producing an adenovirus with a targeting ligand-fiber conjugate. Such a ligand renders adenovirus to have a new tropism and infection specificity, thus improving transduction efficiency. FIGS. 3 and 4 show an embodiment of targeting of adenovirus using the genetic targeting method. When conjugating a VSV-G epitope to an adenovirus protein, and preferably, to the carboxy terminus of the adenovirus fiber, a linker is preferably linked between the adenovirus fiber and the VSV-G epitope to obtain a suitable 3D configuration. The linker is preferably composed of about 5 to about 15 amino acids, in which the amino acids may be any one selected from natural amino acids and chemically synthesized amino acids, and also amino acid derivatives known in the art. In general, amino acids having a small R group, for example, glycine and alanine, are suitable. Amino acids such as serine having hydrophilic R-group, such as serine, are also suitable. In accordance with a more preferred aspect of the present invention, the linker consists of about 5 to about 12 glycine residues.

In accordance with a specific preferred aspect of the present invention, there is provided a recombinant adenovirus YCI-Ad-VSVG (KFCC-11215) having a linker consisting of 8 glycine residues between the terminal end of the adenovirus fiber and a VSV-G epitope. YCI-Ad-VSVG has been deposited under accession number KCCM-10423 on Sep. 14, 2002, at the Korean Culture Center of Microorganisms (KCCM), 361-221, Yurim B/D, Hongje-l-dong, Seodaemun-gu, Seoul 120-091, Republic of Korea.

According to the genetic targeting method, a recombinant virus according to the present invention is produced by constructing a shuttle vector containing a fragment of adenoviral gene and a DNA fragment encoding a protein containing a VSV-G epitope linked thereto, obtaining a recombinant adenovirus plasmid through homologous recombination between the shuttle vector and an adenoviral vector, and transforming or transfecting a suitable cell using the recombinant adenovirus plasmid. In Example 3, targeting of adenovirus using the genetic method is exemplified by the construction of a recombinant adenoviral vector pYCI-Ad-VSVG and production of a recombinant adenovirus YCI-Ad-VSVG. A plasmid useful in constructing a shuttle vector containing a part of the adenoviral genome as well as a nucleotide sequence encoding a protein containing a VSV-G epitope may be prokaryotic or eukaryotic, or known in the art or commercially available. In addition, a host cell for a recombinant plasmid, useful for production of a recombinant adenovirus, is well known to those of ordinary skill in the art, and exemplified by human embryo kidney cell line 293 (E1A/B+) transformed with a nucleotide sequence nt 1-4344 of Ad5, and human embryo retinoblastoma cell 911 containing a nucleotide sequence nt 79-5789 of Ad5.

The recombinant adenovirus according to the present invention is much more effective in killing various tumor cells, including liver cancer, ovarian cancer, breast cancer, brain cancer and lung cancer, than the conventional recombinant adenoviruses.

In another aspect of the present invention, there is provided a pharmaceutical composition comprising: (a) a therapeutically effective amount of a recombinant adenovirus comprising a protein containing a VSV-G epitope derived from vesicular stomatitis virus, which is prepared by introducing the protein into an adenovirus; and (b) a pharmaceutically acceptable carrier.

In another aspect of the present invention, there is also provided a pharmaceutical composition with antitumor effect comprising: (a) a therapeutically effective amount of a replication-competent recombinant adenovirus comprising a protein containing a VSV-G epitope derived from vesicular stomatitis virus, which is prepared by introducing the protein into an adenovirus containing an E1A gene; and (b) a pharmaceutically acceptable carrier. Since the replication-competent recombinant adenovirus has oncolytic effects on various tumor cells, such a pharmaceutical composition is useful in treating tumor-related diseases, including stomach cancer, lung cancer, breast cancer, ovarian cancer, liver cancer, bronchogenic cancer, nasopharyngeal cancer, laryngeal cancer, pancreatic cancer, bladder cancer, colon cancer, and uterine cervical cancer.

In another aspect of the present invention, there is further provided a pharmaceutical composition comprising: (a) a therapeutically effective amount of a replication-incompetent recombinant adenovirus comprising a protein containing a VSV-G epitope derived from vesicular stomatitis virus, which is prepared by introducing the protein into an E1A-deleted or mutated adenovirus, and one or more therapeutic genes; and (b) a pharmaceutically acceptable carrier. Since the therapeutic gene introduced into the replication-incompetent recombinant adenovirus is expressed in target cells, such a pharmaceutical composition is useful in treating cancer and other diseases. For example, the pharmaceutical composition of the present invention is useful for treatment of colorectal cancer and melanoma when HLA-B7 is used as a therapeutic gene, breast cancer and lung cancer when IL-2 is used, neuroblastoma when IFN is used, renal cell carcinama when GM-CSF is used, terminal breast cancer and ovarian cancer when MDR-1 is used, and brain cancer, head and neck cancer, ovarian cancer and mesothelioma when HSV is used. In addition, when the therapeutic gene is a polynucleotide associated with therapy of infectious diseases and malignant and inflammatory diseases and states, the pharmaceutical composition of the present invention is useful for treatment of diseases corresponding to known effects of the polynucleotide, which are, but are not limited to, exemplified by cystic fibrosis, adenosine deaminase deficiency, and AIDS and other infectious diseases, as described above. Such a therapeutic gene is known to those of ordinary skill in the art, and it will be understood that the therapeutic gene can be suitably utilized in the present invention.

Owing to infection independent of CAR distributed on a broad range of cells in the host, the recombinant adenovirus according to the present invention is beneficial in terms of effectively delivering therapeutic genes to cells expressing a very small amount of CAR or none at all. Examples of the cells include blood cells (e.g., leukocytes, such as T cells, B cells, eosinophils or neutrophils, erythrocytes, platelets), lymphocytes, fibrocytes, pulmonary macrophages, and muscle cells in matured bone tissues. Therefore, the pharmaceutical composition comprising the recombinant adenovirus according to the present invention is useful for treatment of damage to the above-mentioned cells and diseases related to the cell damage. For example, hematopoietic growth factors, including EPO, G-CSF, GM-CSF, CSF-1, IL-1, IL-2, IL-3, IL-4, IL-5, IL-6, IL-7, IL-8, IL-9, IL- 10, IL-11, IGF-1 and LIF, and DNA sequences thereof are well known in the art, and the pharmaceutical composition comprising a recombinant adenovirus containing one or more selected from nucleotide sequences encoding the hematopoietic growth factors may be useful for treatment of hematopoietic disorders.

The term "treatment", as used herein, refers to a perfect cure, suppression or alleviation of diseases or disorders. Therefore, the term "therapeutically effective amount", as used herein, means an amount sufficient to achieve the pharmaceutical effect described above.

The pharmaceutically acceptable carrier contained in the pharmaceutical composition of the present invention, which is commonly used in pharmaceutical formulations, but is not limited to, includes lactose, dextrose, sucrose, sorbitol, mannitol, starch, rubber arabic, potassium phosphate, arginate, gelatin, potassium silicate, microcrystalline cellulose, polyvinylpyrrolidone, cellulose, water, syrups, methyl cellulose, methylhydroxy benzoate, propylhydroxy benzoate, talc, magnesium stearate, and mineral oils. The pharmaceutical composition according to the present invention may further include a lubricant, a humectant, a sweetener, a flavoring agent, an emulsifier, a suspending agent, and a preservative.

The pharmaceutical composition according to the present invention may be administered through the routes used commonly in gene therapy, and preferably, administered parenterally, i.e., by intravenous, intraperitoneal, intramuscular, subcutaneous, or local administration. For example, the pharmaceutical composition may be administered intraperitoneally to treat ovarian cancer and intravenously to treat liver cancer, directly injected to visible tumor mass to treat breast cancer, directly injected to enema to treat colon cancer, and directly injected to a catheter to treat bladder cancer.

A suitable dosage amount of the pharmaceutical composition of the present invention may vary depending on pharmaceutical formulation methods, administration methods, the patient's age, body weight, sex, pathogenic state, diet, administration time, administration route, an excretion rate and sensitivity for a used pharmaceutical composition, and doctors of ordinary skill in the art can determine an effective amount of the pharmaceutical composition for desired treatment. Generally, the pharmaceutical composition of the present invention comprises $5 \times 10^{10}$ to $5 \times 10^{10}$ pfu/ml of a recombinant adenovirus, and $1 \times 10^{10}$ pfu of a recombinant adenovirus is typically injected once per two days over two weeks.

The pharmaceutical composition comprising a recombinant adenovirus according to the present invention may be formulated into a unit dose formulation using a pharmaceutically acceptable carrier and/or excipient, or a multidose formulation by being contained in a multidose container. The pharmaceutical composition may be formulated into extracts, powder, granules, tablets or capsules, and further include a dispersion agent or a stabilizer, and the pharmaceutical composition may be solutions of oil or aqueous medium, suspensions or emulsions.

The pharmaceutical composition comprising a recombinant adenovirus according to the present invention may be utilized alone or in combination with typical chemotherapy or radiotherapy. Such combination therapy may be more effective in treating cancer. The chemotherapeutic agent useful for the combination therapy include cisplatin, carboplatin, procarbazine, mechlorethamine, cyclophosphamide, ifosfamide, melphalan, chlorambucil, bisulfan, nitrosourea, dactinomycin, daunorubicin, doxorubicin, bleomycin, plicomycin, mitomycin, etoposide, tamoxifen, taxol, transplatinum, 5-fluorouracil, vincristin, vinblastin and methotrexate. Examples of the radiotherapy useful for the combination therapy include X-ray illumination and γ-ray illumination.

In order to increase stability at room temperature, reduce the need for high-cost storage at low temperature, and prolong shelf-life, the pharmaceutical composition comprising a recombinant adenovirus according to the present invention may be lyophilized. A process for freeze-drying may comprise the steps of freezing, first drying and second drying. After freezing, the composition is heated under pressure to evaporate vapor. At the second drying step, residual water is removed from the dry product.

For preparation of DNA vaccine, freeze-drying of the pharmaceutical composition according to the present invention may be achieved according to the following steps: (1) determining collapse temperature of the pharmaceutical composition through a freeze-drying microscopic analysis (Pikal, M. J. et al., Int. J. Pharm. 62, 165-186, 1990); (2) placing a vial on the shelf of a freeze-drier at room temperature and then equilibrating it for about 30 min at −1° C.; (3) cooling the shelf to −55° C. and then maintaining it at −55° C. for 2 hrs; (4) performing a first drying at about −32° C. of product temperature or 5° C. lower temperature than the collapse temperature; (5) performing a second drying at 35° C. under pressure of 55 to 120 mmHg; and (6) covering the vial with the lid under vacuum condition of the freeze-drier, and storing it at 2 to 8° C. after crimp-sealing.

The freeze-dried pharmaceutical formulation may include an excipient and a lyoprotectant. Non-limiting examples of the excipient include a buffer solution containing 0.9% NaCl and 10 mM sodium phosphate (pH 7.0) or 10 mM sodium citrate (pH 7.0). The lyoprotectant functions to protect biological molecules contained in the composition during the freeze-drying, and supply mechanical support to the final product, which is exemplified by PBS (pH 7.0), and PBS/4%, 12% or 15% trehalose.

The present invention will be explained in more detail with reference to the following examples in conjunction with the accompanying drawings. However, the following examples are provided only to illustrate the present invention, and the present invention is not limited to them.

EXAMPLE 1

Preparation of an E1B-55 kDa-deleted Recombinant Adenovirus

Figure 10:
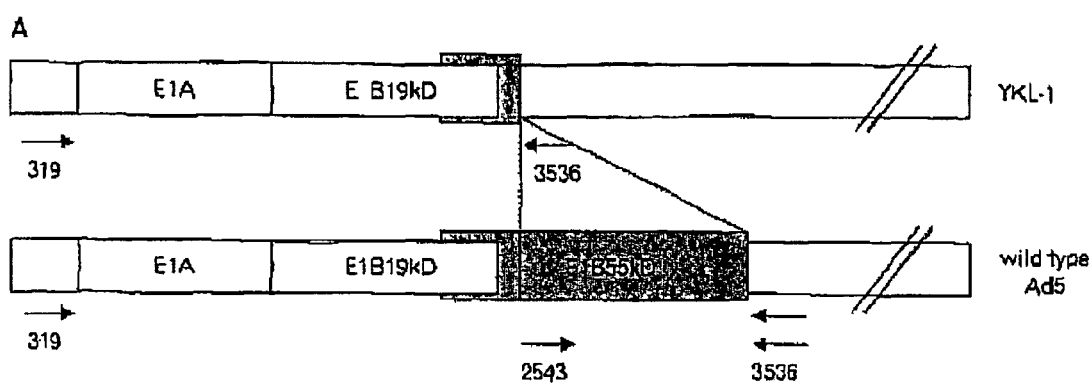
FIG. 10 is a schematic representation of a characteristic part of the construction of the recombinant adenovirus YKL-1.

To delete only the open reading frame of E1B-55 kDa protein from the adenovirus E1 gene, after designing primers capable of amplifying a part of E1A1 gene containing ORFs for E1A and E1B-19 kDa, polymerase chain reaction (PCR) was performed using pXC1 (Microbis, Ontario, Canada) as a DNA template, and a sense primer 5'-TTATTGGATCCTTTGTCTAGGGCCGCGGG-3' (SEQ ID NO: 1) containing a BamHI restriction site at its end, and an anti-sense primer 5'-TCTTGGATCCAGATCTATACAGTTAAGCCACCTATACAAC-3' (SEQ ID NO: 2) containing a BamHI restriction site and a BglII restriction site at the ends and two stop codons by substitution at nt 2253 (C::T) and nt 2262 (G::T). As a result, a PCR product comprising nt 343-2270 of the adenovirus genome was obtained (FIG. 10).

The PCR product of 1.9 kb was digested with BamHI and then inserted into a BglII site of E1 gene-deleted pCA14 (Microbis, Ontario, Canada). After digesting the resulting shuttle vector pCA14-E1A/E1B-19 kDa with XmnI, *E. coli* BJ5183 was transformed with the shuttle vector along with an E1/E3 gene-deleted adenovirus vector vmd1324Bst digested with BstB1(Dr. Verca, University of Fribourgh, Switzerland) to induce homologous recombination between the two vectors (FIG. 10), giving a recombinant adenoviral pYKL-1 vector. pYKL-1 DNA was isolated from the transformed *E. coli* and digested with HindIII, confirming that the 55 kDa E1B segment had been deleted from pYKL-1. Thereafter, 293 cells were transfected with PacI-digested linear pYKL-1 to produce an E1B-55 kDa-deleted recombinant adenovirus. The produced recombinant adenovirus was designated as YKL-1, and deposited in Korean Culture Center of Microorganisms (KCCM) with the accession No. KCCM-10424 on Sep. 19, 2002.

EXAMPLE 2

Figure 11:
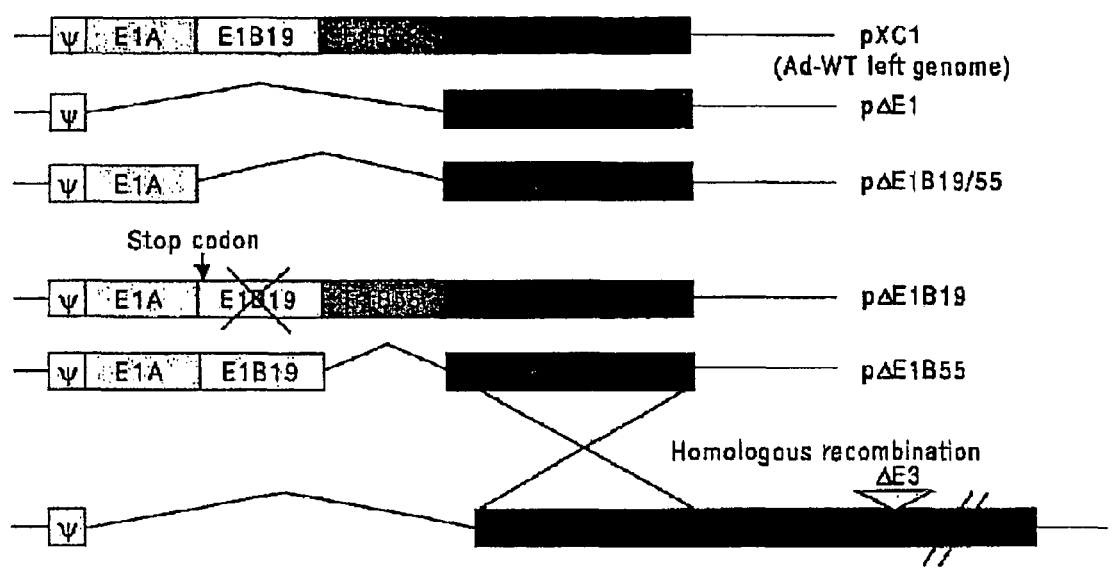
FIG. 11 is a schematic representation of a characteristic part of the construction of each of E1B-mutated adenoviruses Ad-ΔE1B19, Ad-ΔE1B55 and Ad-ΔE1B19/55 as well as Ad-ΔE1 and Ad-WT.

Preparation of an E1B-19 kDa or E1B-19 kDa/E1B-55 kDa-deleted Recombinant Adenovirus To construct a recombinant adenovirus shuttle vector pΔE1B19/55 with E1B-19 kDa and E1B-55 kDa genes deleted, a primer set capable of giving a PCR product containing only an E1A gene was designed first, and PCR was carried out using an adenovirus E1 shuttle vector pXC1 (Microbix, Ontario, Canada) as a DNA template and the primer set composed of a sense primer 5'-TTATTGGATCCTTTGTCTAGGGCCGCGGG-3' (SEQ ID NO: 3) and an antisense primer 5'-CCAGGAT CCAGATCTCCCCATTTAACACGCCATGC-3' (SEQ ID NO: 4). The amplified PCR product was digested with BamHI and inserted to the BglII site of pCA14, thus giving a shuttle vector pΔE1B19/55. Separately, to construct a shuttle vector pΔE1B19 kDa carrying an E1B-19 kDa gene in which the start codon is substituted with a stop codon, a DNA fragment of 1.3 kb prepared by digesting pXC1 with XbaI and BamHI restriction enzymes was subcloned to a cloning vector pSP72 (Promega, USA), and site directed mutagenesis (Stratagene, La Jolla, Calif., USA) was performed on the subcloned DNA fragment using a sense primer 5'-GTTACATCTGACCT CCTGTAGGCTAGCGAGTGTTTGGAAG-3' (SEQ ID NO: 5) and an antisense primer 5'-CTTCCAAACACTCGCTAGCCTACAGGAGGTCAGATGTAAC-3' (SEQ ID NO: 6), of which one contains a mutation in which a start codon is substituted with a stop codon. As a result of the mutagenesis, the produced pSP72/pXC1/1.3 kb/A19 mt plasmid was confirmed to have a mutation through DNA sequencing. Thereafter, the pXC1/1.3 kb/Δ19 mt plasmid was digested with XbaI and BamHI and then subcloned to XbaI and BamHI sites of pXC1, thus producing a shuttle vector pΔE1B19 kDa. According to the same method as in Example 1, the shuttle vectors pΔE1B19/55 and pΔE1B191Da were digested with XmnI, and each of the two shuttle vectors was introduced into *E. coli* BJ5183 along with BstBI-digested single-strand adenovirus vmd1324Bst (Dr. Verca, University of Fribourgh, Switzerland) to induce homologous recombination between the two vectors (FIG. 11). Plasmid DNA was then isolated from the transformed *E. coli* and digested with HindIII. As a result, it was found that an Ad-pΔE1B plasmid with both E1B-19 kDa and E1B-55 kDa genes deleted, and an Ad-pΔE1B19 plasmid with an E1B-19 kDa insert in which a start codon is substituted with a stop codon were produced. Thereafter, 293 cells were transfected with each of the two recombinant adenoviral vectors digested with PacI to produce Ad-pΔE1B19/55 and Ad-pΔE1B19 recombinant adenoviruses. A recombinant adenovirus with an E1B-19 kDa gene deleted was designated as YKC-1, and deposited in the Korean Culture Center of Microorganisms (KCCM) with the accession No. KCCM-10425 on Sep. 19, 2002.

EXAMPLE 3

Preparation of Recombinant Adenoviruses

A. Preparation of a Recombinant Adenovirus YCI-Ad-VSVG

Retargeting of adenovirus was performed in such a way that an epitope consisting of 19 amino acids, derived from the envelope glycoprotein of vesicular somatitis virus (VSV-G), was introduced to the YKL-1 adenovirus with a gene encoding an E1B-55 kDa protein deleted, prepared in Example 1, as follows (FIGS. 1, 2, 3 and 4).

Figure 12:
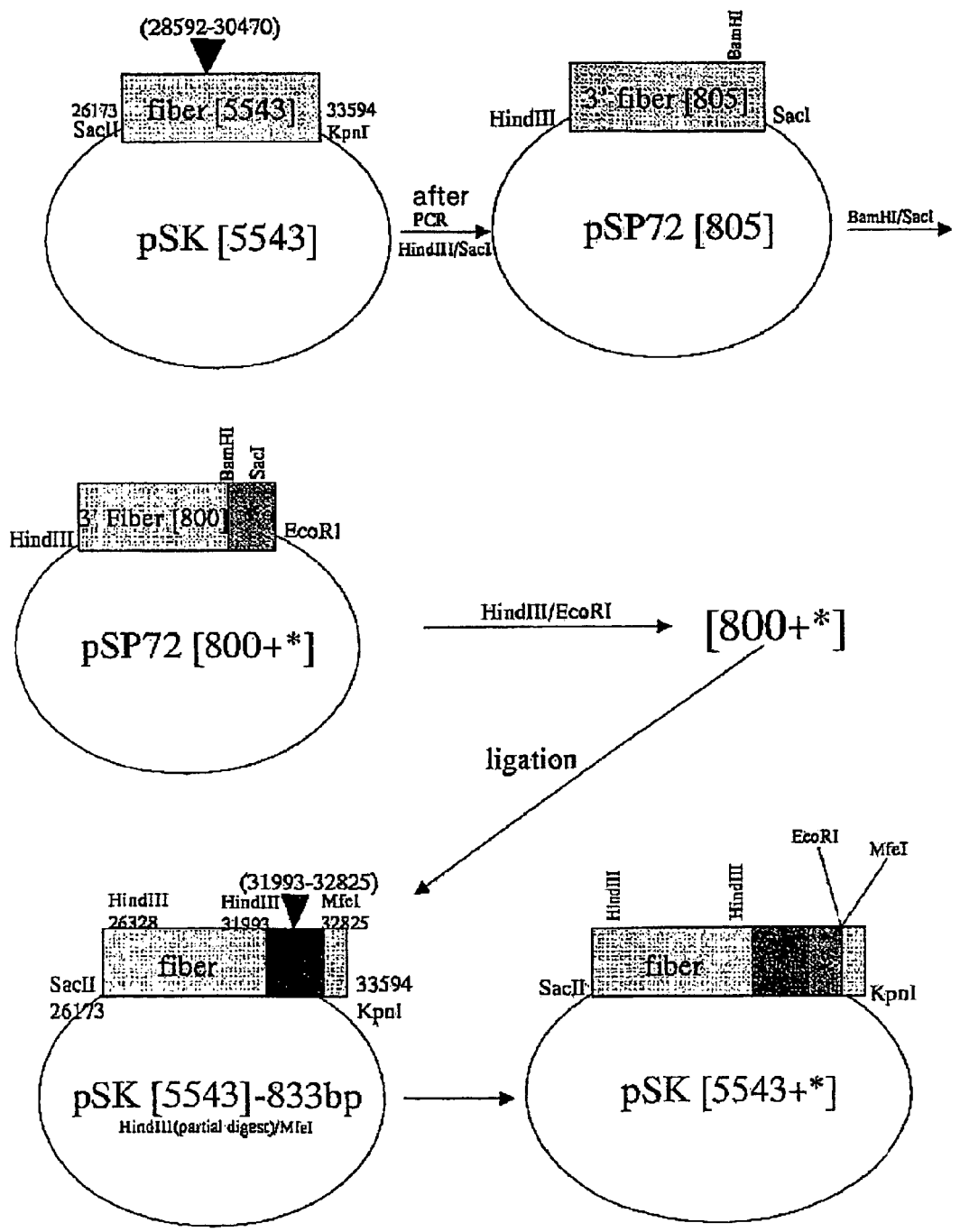
FIG. 12 is a process for construction of the recombinant adenovirus YCI-Ad-VSVG according to the present invention.

First, an adenoviral shuttle vector was prepared. A DNA fragment of 5543 bp from vmd1324Bst, which contained a gene encoding the adenovirus fiber protein, was digested with SacII and KpnI, and subcloned to the SacII and KpnI-digested pBluescript SK plasmid (Stratagene, Canada), thus producing of a recombinant vector pSK[5543] (FIG. 12).

In order to reclone the 3' end region of the fiber, PCR was performed using pSK[5543] as a DNA template and a primer set composed of a sense primer 5'-GGCCTTTACTTGTTTA-CAGC-3' (SEQ ID NO: 7) and an antisense primer 5'-GGG-GAGCTCGGATCCTCCTTCTTGGGCAATGTATG-3' (SEQ ID NO: 8). The antisense primer was designed to substitute a stop codon (TTA) with a codon encoding Gly (TCC), thus removing a stop codon from the C-teminus of the fiber, and having BamHI and SacI restriction sites.

In detail, PCR was carried out with 100 ng of the DNA template and 10 ng of the primer set. PCR conditions included denaturation at 94° C. for 2 min, and 30 cycles of denaturation at 94° C. for 1 min, annealing at 55° C. for 1 min and elongation at 72° C. for 1 min, followed by final elongation at 72° C. for 10 min. A PCR product of about 850 bp was digested with HindIII and SacI, and was inserted into HinIII and SacI sites of a cloning vector pSP72 (Promega, USA), thus giving pSP72[805] (FIG. 12).

Further, a VSV-G epitope known to participate in entry of VSV into host cells consists of 19 amino acids ranging from 118 to 136, and its amino acid sequence and its corresponding nucleotide sequence were as follows: GTWLNPGFP-PQSCGYATVT (SEQ ID NO: 9); and 5'-GGAACTTG-GCTG AATCCAGGCTTCCCTCCTCAAA GTTGTG-GATATGCAACTGTGACG-3' (SEQ ID NO: 10).

In order to obtain suitable spatial configuration of the epitope when being incorporated to the carboxy terminus of the adenovirus fiber, a nucleotide sequence encoding a linker consisting of 8 glycine residues was inserted between the nucleotide sequences encoding the epitope and the fiber, as follows. To insert a DNA fragment encoding 8 Gly to the pSP72[805] vector, based on the known nucleotide sequences corresponding to both the linker and the VSV-G epitope, a single-stranded oligonucleotide coding both the linker and the VSV-G epitope was synthesized, which contained a BamHI site at 5' end and a SacI site at 3' end, and had a nucleotide sequence as follows:

oligomers were incubated at 37° C. for 5 min to allow to form a hybrid. In addition, to amplify the hybrid, a primer set of 27-mers was prepared: a sense primer: 5'-GAA/GGG/GGA/TCC/GGC/GGG/GGC/GGT/GGA-3' (SEQ ID NO: 12); and an antisense primer 5'-CCC/GAG/CTC/ACG/TCA/CAG/TTG/CAT/ATC-3' (SEQ ID NO: 13).

PCR was performed according to the above-mentioned conditions, using 10 ng of the primer set and 100 ng of the hybrized oligomer as a DNA template. The amplified PCR product was digested with BamHI and SacI, and the resulting DNA fragment of 103 bp was subcloned to BamHI and SacI-digested pSP72[805] vector, thus generating pSP72[805+103 bp] (FIG. 12).

Thereafter, the pSP72[805+103 bp] vector was cleaved with HindIII and EcoRI to produce a fragment [805+103 bp] containing portions of the adenovirus fiber and the VSV-G epitope linked thereto. The shuttle vector pSK[5543], carrying a nucleotide sequence encoding the adenovirus fiber, was digested with HindIII and MfeI, and the resulting fragment of about 833 bp was then replaced with the fragment [805+103 bp], thereby producing an adenovirus shuttle vector pSK[5510+103 bp] (FIG. 12).

Figure 6:
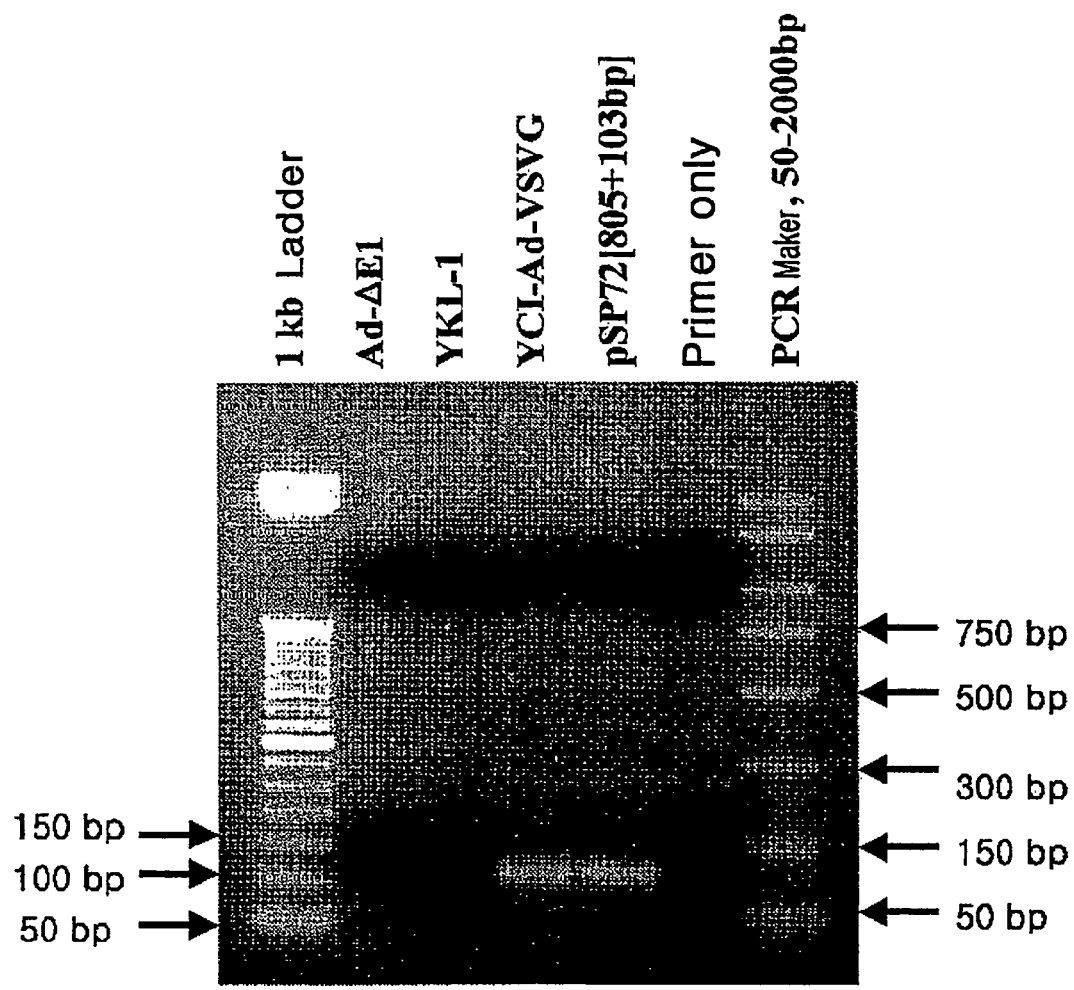
FIG. 6 is a photograph showing a result of PCR to confirm incorporation of a VSV-G epitope into the fiber of the recombinant adenovirus YCI-Ad-VSVG.
Figure 7A:
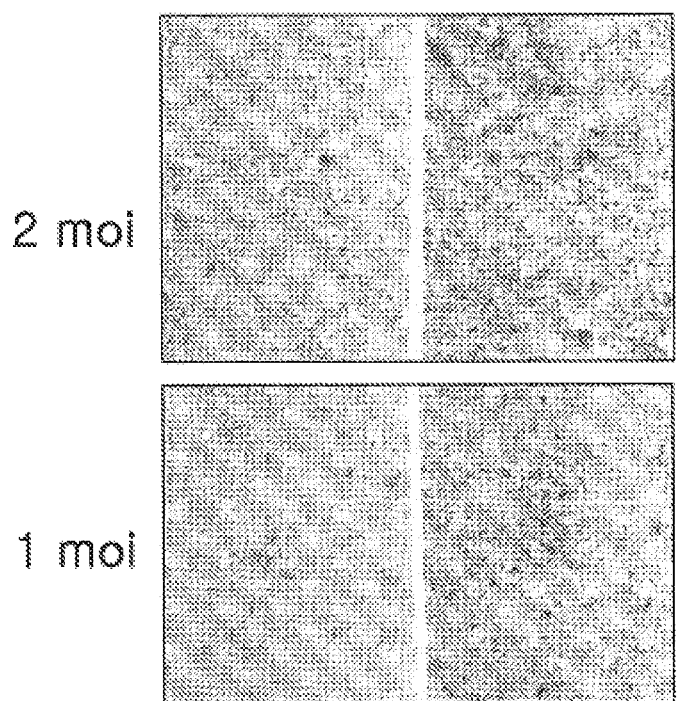
FIG. 7a is a photograph showing increased gene transfer efficiency of the recombinant adenovirus dl324-LacZ-VSVG to U343 cells.
Figure 7B:
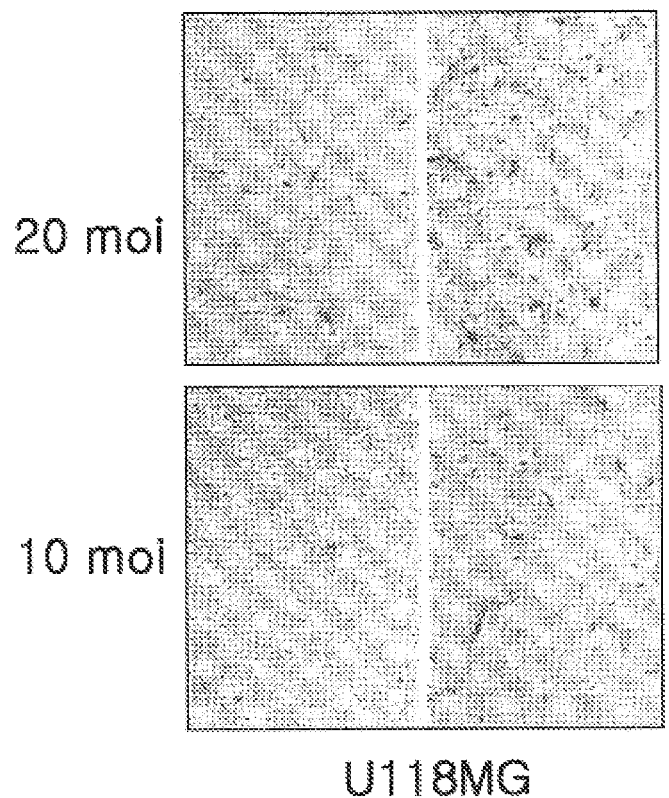
FIG. 7b is a photograph showing increased gene transfer efficiency of the recombinant adenovirus dl324-LacZ-VSVG to U118MG cells.
Figure 7C:
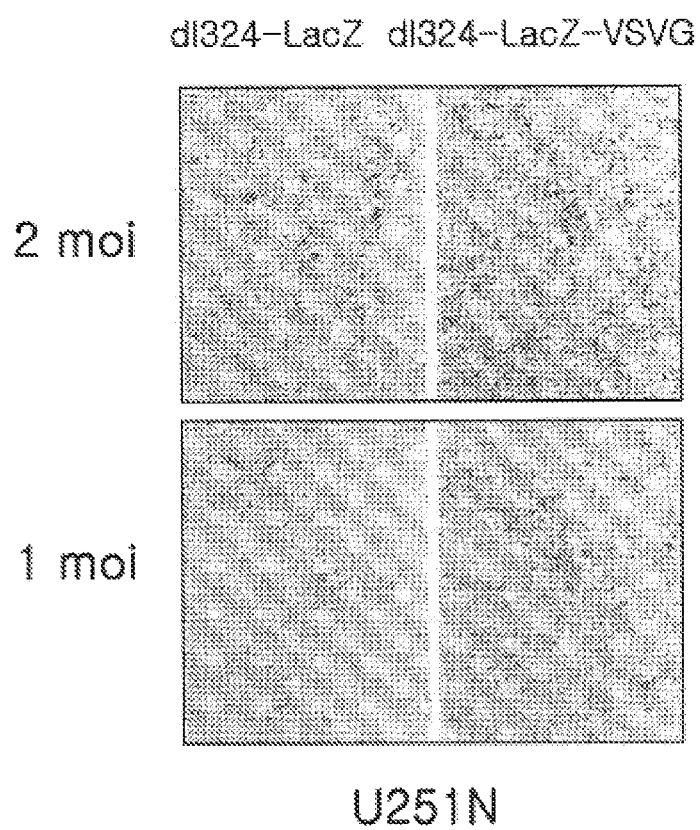
FIG. 7c is a photograph showing increased gene transfer efficiency of the recombinant adenovirus dl324-LacZ-VSVG to U251N cells.
Figure 7D:
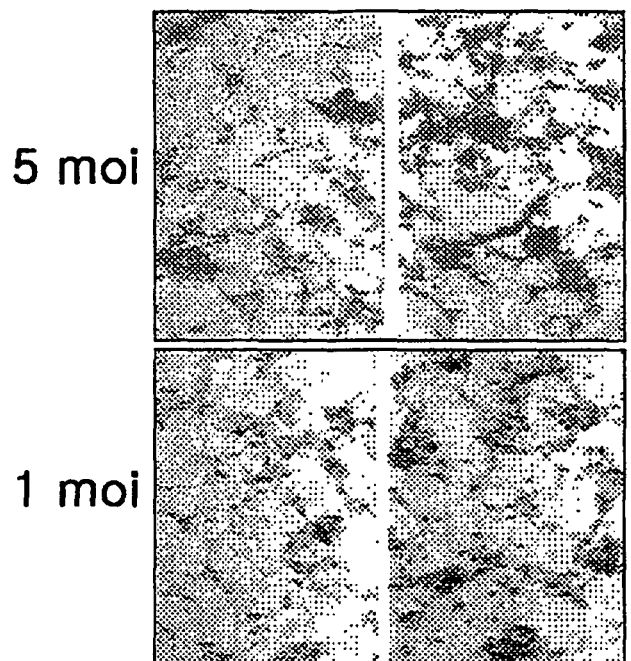
FIG. 7d is a photograph showing increased gene transfer efficiency of the recombinant adenovirus dl324-LacZ-VSVG to U87MG cells.
Figure 7E:
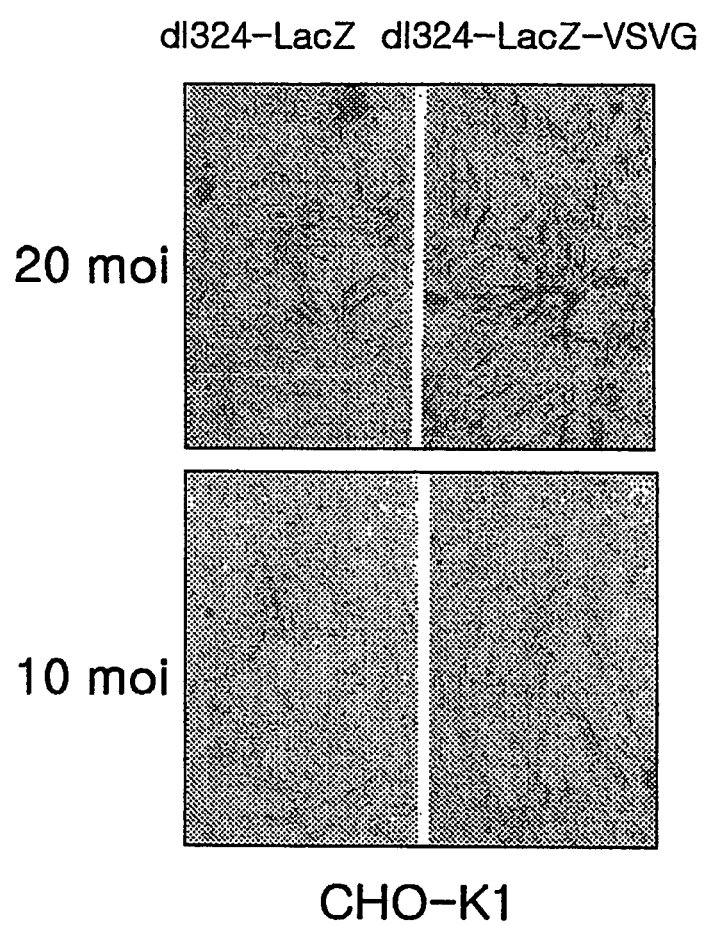
FIG. 7e is a photograph showing increased gene transfer efficiency of the recombinant adenovirus dl324-LacZ-VSVG to CHO-K1 cells.
Figure 7F:
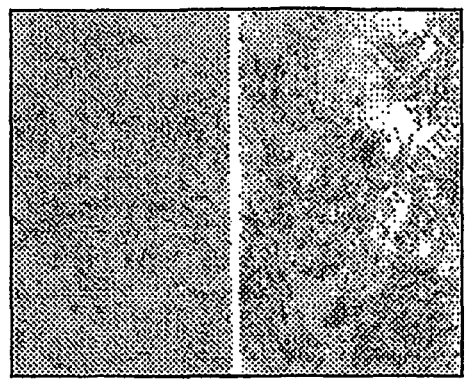
FIG. 7f is a photograph showing increased gene transfer efficiency of the recombinant adenovirus dl324-LacZ-VSVG to Lec2 cells.
Figure 7F:
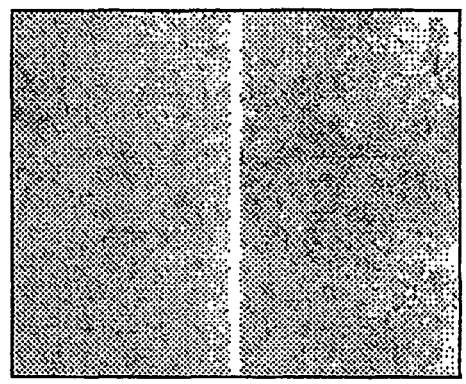
Figure 7G:
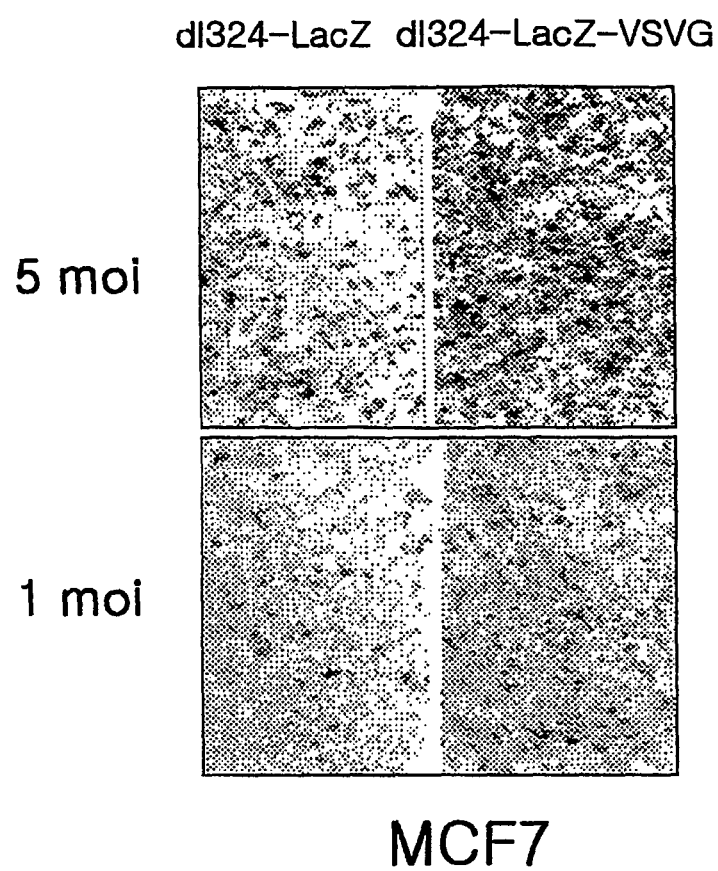
FIG. 7g is a photograph showing increased gene transfer efficiency of the recombinant adenovirus dl324-LacZ-VSVG to MCF-7 cells.
Figure 7H:
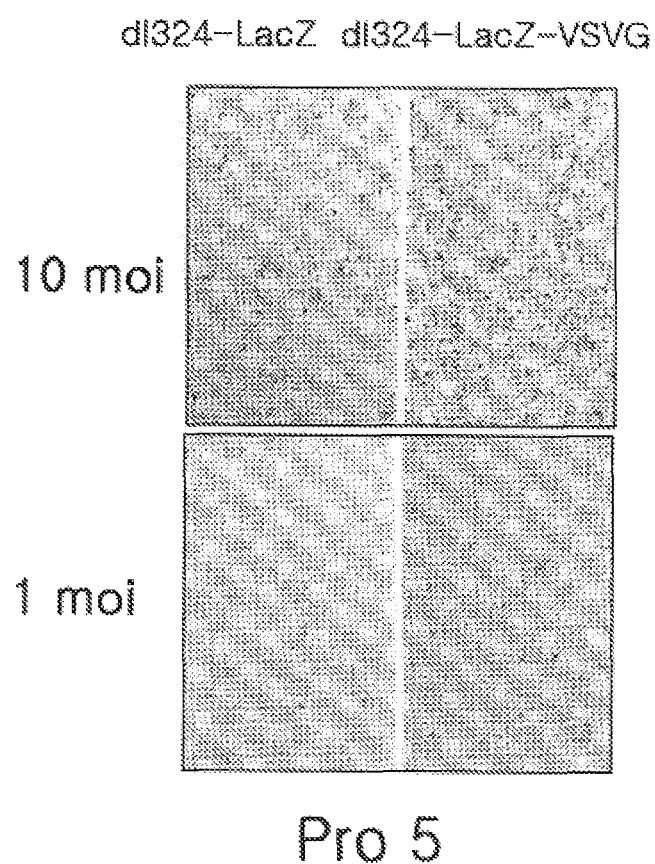
FIG. 7h is a photograph showing increased gene transfer efficiency of the recombinant adenovirus dl324-LacZ-VSVG to Pro5 cells.
Figure 8A:
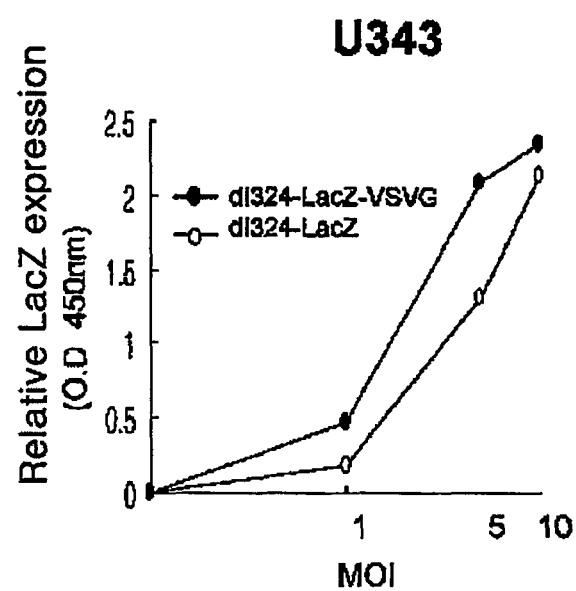
FIG. 8a is a graph showing increased gene transfer efficiency of the recombinant adenovirus dl324-LacZ-VSVG to U343 cells.
Figure 8B:
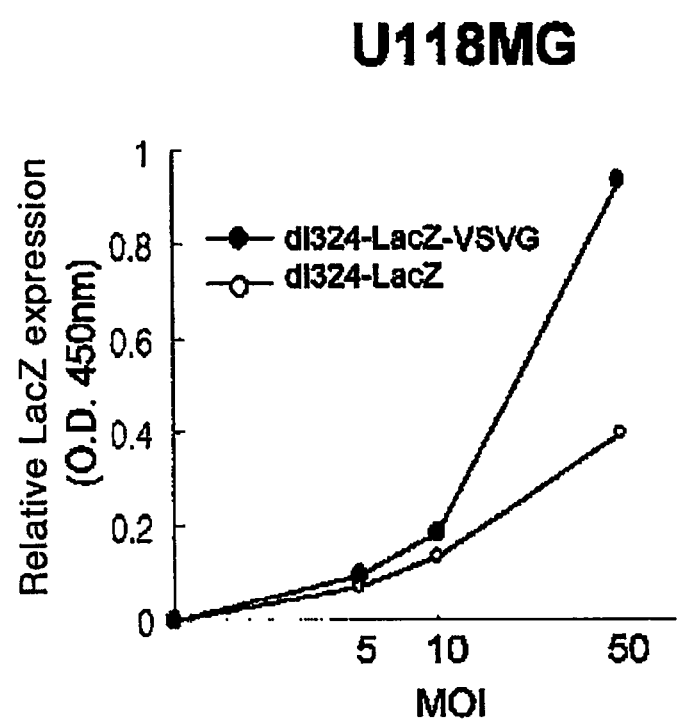
FIG. 8b is a graph showing increased gene transfer efficiency of the recombinant adenovirus dl324-LacZ-VSVG to U 118MG cells.
Figure 8C:
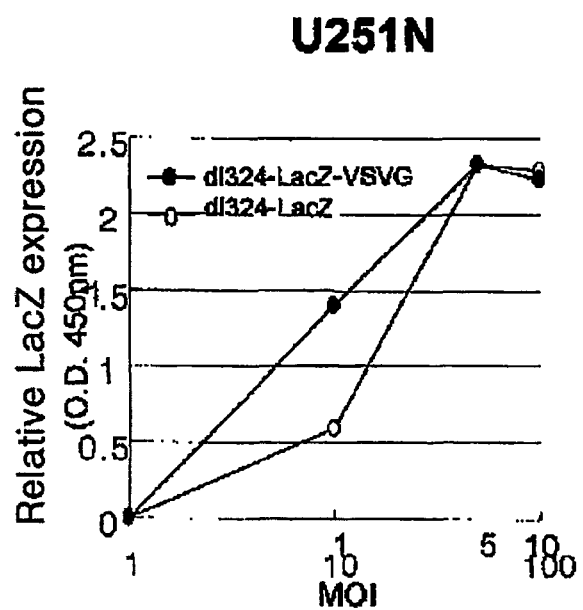
FIG. 8c is a graph showing increased gene transfer efficiency of the recombinant adenovirus dl324-LacZ-VSVG to U251N cells.
Figure 8D:
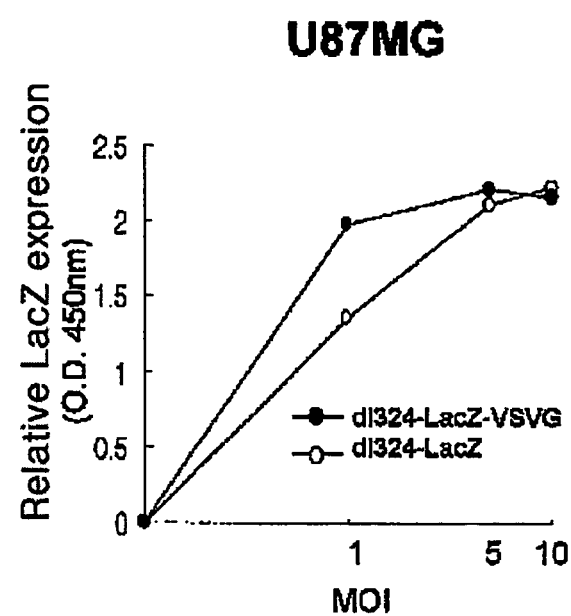
FIG. 8d is a graph showing increased gene transfer efficiency of the recombinant adenovirus dl324-LacZ-VSVG to U87MG cells.
Figure 8E:
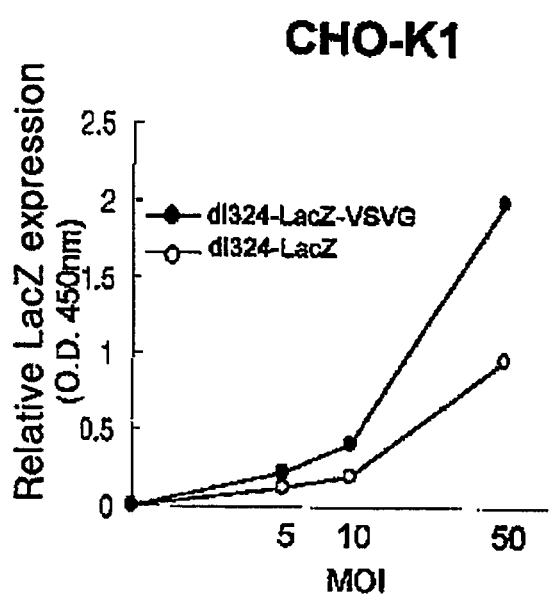
FIG. 8e is a graph showing increased gene transfer efficiency of the recombinant adenovirus dl324-LacZ-VSVG to CHO-K1 cells.
Figure 8F:
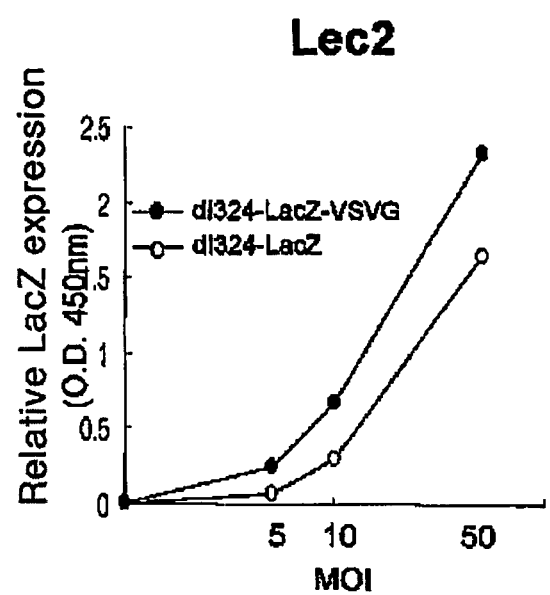
FIG. 8f is a graph showing increased gene transfer efficiency of the recombinant adenovirus dl324-LacZ-VSVG to Lec2 cells.
Figure 8G:
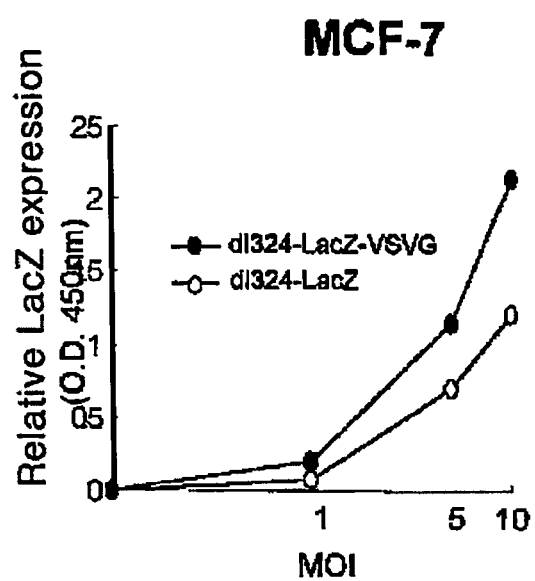
FIG. 8g is a graph showing increased gene transfer efficiency of the recombinant adenovirus dl324-LacZ-VSVG to MCF-7 cells.
Figure 8H:
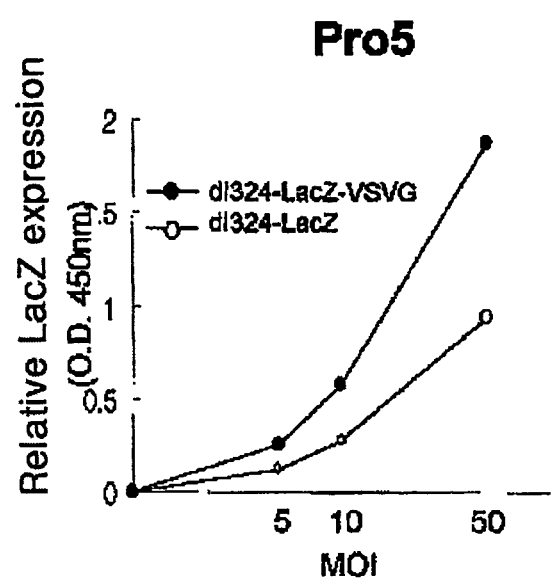
FIG. 8h is a graph showing increased gene transfer efficiency of the recombinant adenovirus dl324-LacZ-VSVG to Pro5 cells.
Figure 9A:
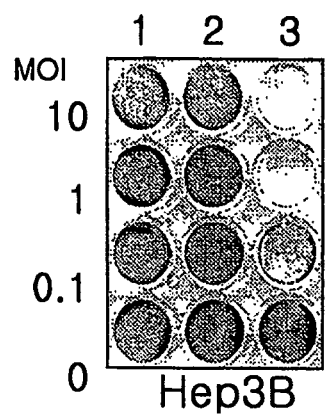
FIG. 9a is a photograph showing increased tumor cell-killing effect of the recombinant adenovirus YCI-Ad-VSVG on Hep3B cells through cell lesion analysis, wherein 1=ΔE1, 2=YKL-1, and 3=YCI-Ad-VSVG.
Figure 9B:
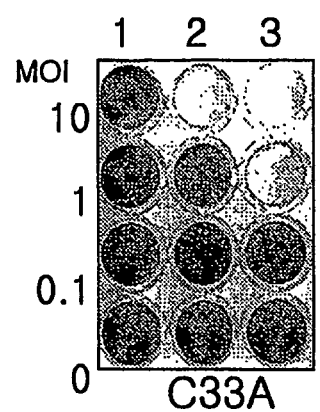
FIG. 9b is a photograph showing increased tumor cell-killing effect of the recombinant adenovirus YCI-Ad-VSVG on C33A cells through cell lesion analysis, wherein 1=Δb E1, 2=YKL-1, and 3=YCI-Ad-VSVG.
Figure 9C:
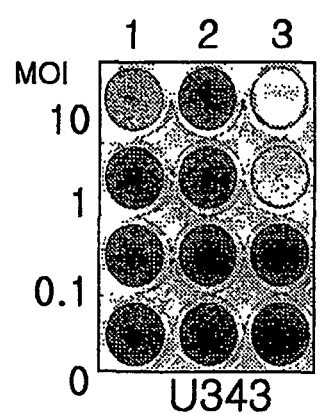
FIG. 9c is a photograph showing increased tumor cell-killing effect of the recombinant adenovirus YCI-Ad-VSVG on U343 cells through cell lesion analysis, wherein 1=ΔE1, 2=YKL-1, and 3=YCI-Ad-VSVG.
Figure 9D:
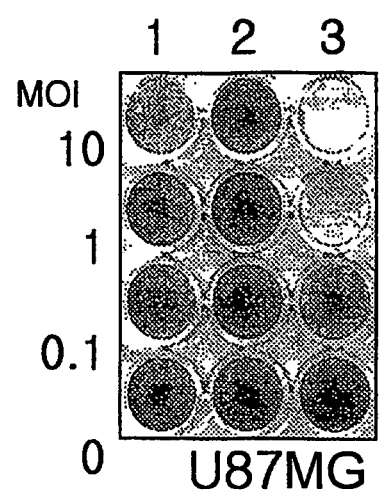
FIG. 9d is a photograph showing increased tumor cell-killing effect of the recombinant adenovirus YCI-Ad-VSVG on U87MG cells through cell lesion analysis, wherein 1=Δb E1, 2=YKL-1, and 3=YCI-Ad-VSVG.
Figure 9E:
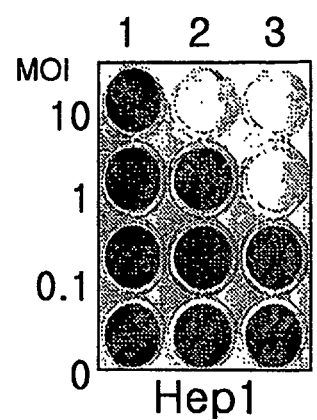
FIG. 9e is a photograph showing increased tumor cell-killing effect of the recombinant adenovirus YCI-Ad-VSVG on Hep1 cells through cell lesion analysis, wherein 1=ΔE1, 2=YKL-1, and 3=YCI-Ad-VSVG.
Figure 9F:
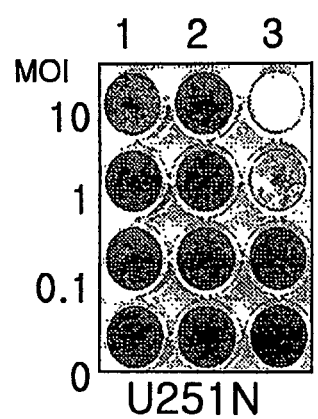
FIG. 9f is a photograph showing increased tumor cell-killing effect of the recombinant adenovirus YCI-Ad-VSVG on U251-N cells through cell lesion analysis, wherein 1=ΔE1, 2=YKL-1, and 3=YCI-Ad-VSVG.
Figure 9G:
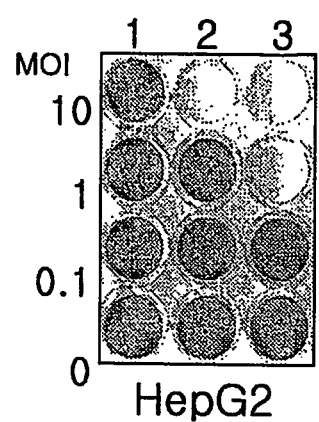
FIG. 9g is a photograph showing increased tumor cell-killing effect of the recombinant adenovirus YCI-Ad-VSVG on HepG2 cells through cell lesion analysis, wherein 1=ΔE1, 2=YKL-1, and 3=YCI-Ad-VSVG.
Figure 9H:
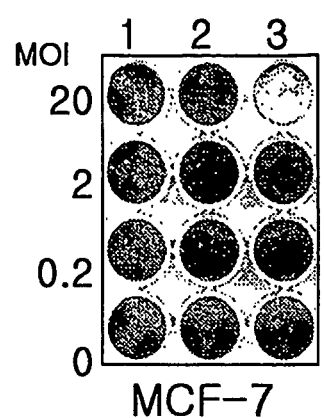
FIG. 9h is a photograph showing increased tumor cell-killing effect of the recombinant adenovirus YCI-Ad-VSVG on MCF-7 cells through cell lesion analysis, wherein 1=ΔE1, 2=YKL-1, and 3=YCI-Ad-VSVG.

After digesting the pYKL-1 plasmid prepared in Example 1 with SpeI, the linearized pYKL-1, together with the shuttle vector pSK[5510+103 bp], was introduced into *E. coli* BJ5183 to induce homologous recombination. After incubation for 1 day, plasmid DNA was then isolated from the transformed *E. coli*. Through PCR using the 27-mer primer set, a DNA fragment of 103 bp was amplified (FIG. 6).

The plasmid DNA demonstrated to carry the 103 bp DNA fragment was introduced again into DH5α (Gibco, USA) having high copy number. The recovered plasmid DNA was analyzed through digestion with PacI to investigate production of a 2 kb fragment and digestion with HindIII. The resulting recombinant adenovirus plasmid was designated as pYCI-Ad-VSVG.

After being digested with PacI, the linearized pYCI-Ad-VSVG plasmid was introduced into 293 cells (Microbix, Canada) to produce recombinant adenoviral virions. As a result of PCR performed using genomic DNA isolated from the produced adenovirus, the 103-bp fragment to the VSV-G epitope was amplified (FIG. 6). The produced adenovirus was designated as YCI-Ad-VSVG, and deposited in the Korean Culture Center of Microorganisms (KCCM) with the accession No. KCCM-10423 on Sep. 19, 2002. This deposit was made under the Budapest Treaty on the International Recognition of the Deposit of Microorganisms, and all restrictions imposed by the depositor on the availability to the public of the deposited material will be irrevocably removed upon the grant of the patent.

B. Preparation of a Recombinant Adenovirus d1324-LacZ-VSVG

To analyze the effect of the incorporation of the VSV-G epitope on transduction efficiency of adenovirus, a LacZ gene was introduced to a replication-incompetent adenovirus, as follows. A pcDNAhygroLacZ plasmid (Invitrogen, USA)

```
5'-GA/TCC/GGC/GGG/GGC/GGT/GGA/GGA/GGG/GGT/GGA/ACT/TGG/ (SEQ ID NO: 11)
CTG/AAT/CCA/GGC/TTC/CCT/CCT/CAA/AGT/TGT/GGA/TAT/GCA/ACT/GTG/
ACG/TGA/GCT-3'.
```

Then, a single-stranded DNA complementary to the sequence of the above oligomer was synthesized using a DNA synthesizer. Thereafter, the two synthesized single-stranded was digested with SpeI and XbaI, thus giving a LacZ fragment, and the LacZ fragment was then subcloned to the adenovirus shuttle vector pCA14 (Microbix, Canada)

digested with XbaI, thus generating a pCA14LacZ plasmid. After digesting the E1/E3-deleted vmd1324Bst (Heider, H. et al., Biotechniques, 28(2):260-265, 268-270, 2000) with BstBI, homologous recombination was induced according to the same procedure as described above, resulting in production of d1324/pCA141LacZ. Next, in order to incorporate the VSV-G epitope into the carboxy terminus of the fiber of the d1324/pCA14/LacZ adenoviral vector, after digesting the shuttle vector pSK[5510+103 bp], carrying a nucleotide sequence encoding the VSV-G epitope, with SacII and KpnI, E. coli BJ5183 was transformed with the linearized shuttle vector and SpeI-digested d1324/pCA14/LacZ to induce homologous recombination between the two vectors. The produced recombinant adenovirus was designated as d1324-LacZ-VSVG. The recombinant adenovirus was grown in 293 cells, and viral titer was determined through limiting dilution or optical density analysis.

C. Gene Constitution Analysis of the E1 Region of the Recombinant Adenovirus YCI-Ad-VSVG Human hepatoma cell line Hep3B (HB-8044, ATCC, USA) was infected with adenovirus Ad-ΔE1 (whole E1-deleted adenovirus), YKL-1, YCI-Ad-VSVG and the wild-type adenovirus Ad-wt, respectively, at 10 multiplicity of infection (MOI). After 2 days, viral genome was isolated using a genomic DNA isolation kit (Qiagen, USA). The replication-incompetent adenovirus Ad-ΔE1 used as a control was prepared using pCA14 (Microbix) as a shuttle vector according to the same procedure in Example 2.

Figure 5:
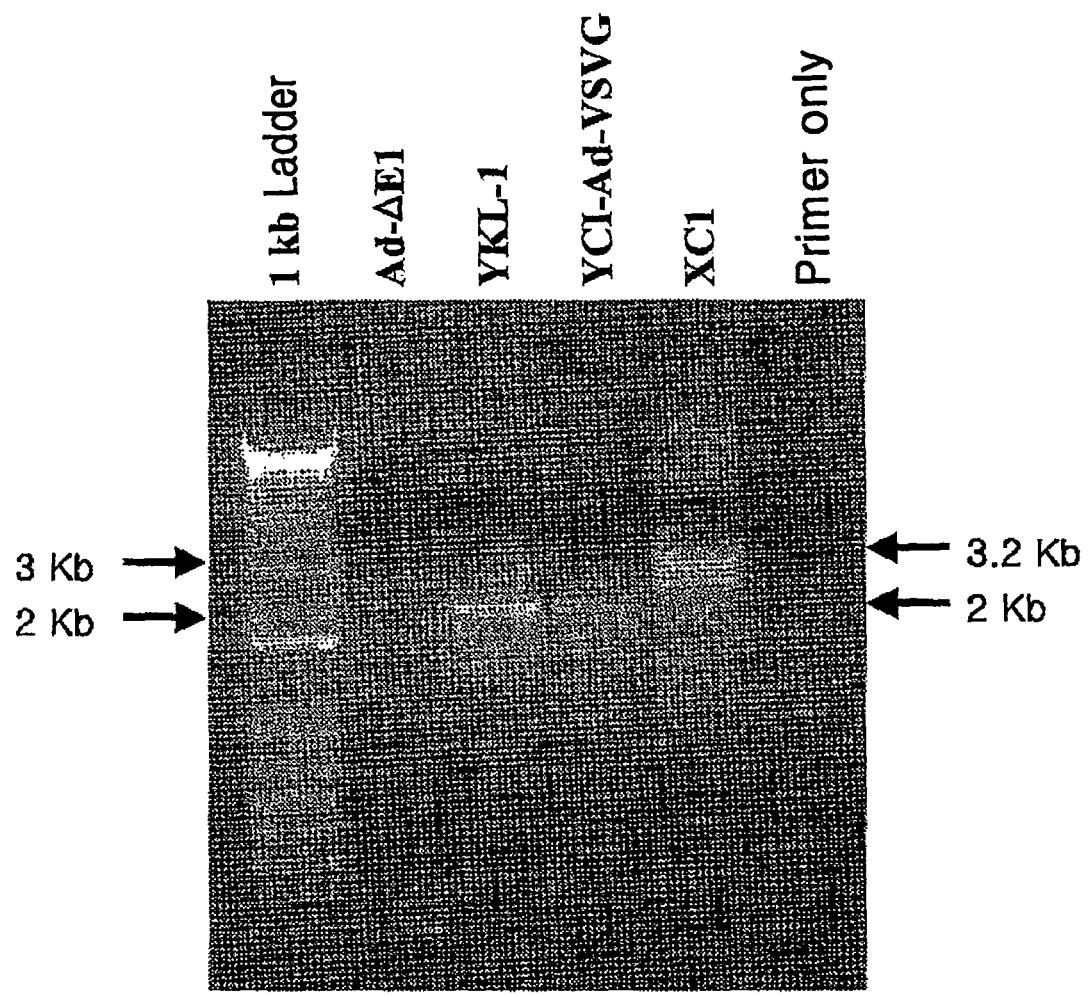
FIG. 5 is a photograph showing PCR products for open reading frames contained in E1 gene contained in the recombinant adenovirus YCI-Ad-VSVG.

Thereafter, an E1 gene was amplified by PCR using each of the isolated viral genomes as a template and a primer set composed of a sense primer: 5'-TTTGTGTTACTCAT-AGCGCGT-3' (SEQ ID NO: 14); and an antisense primer: 5'-ATTCTTTCCCACCCTTAAGCC-3' (SEQ ID NO: 15). The resulting reaction mixtures were electrophoresed on an agarose gel (FIG. 5). As apparent in FIG. 5, because of harboring the same E1 gene as that contained in the YKL-1 adenovirus, in which the E1B-55 kDa gene was selectively deleted, the YCI-Ad-VSVG recombinant adenovirus according to the present invention produced a PCR product of about 2 kb, while an approximately 3.2 kb fragment was found in the wild-type adenovirus with the whole E1 gene encoding E1A, E1B-19 kDa and E1B-55 kDa.

D. Identification of Incorporation of a VSV-G Epitope into the Carboxy Terminus of the Fiber Protein of the Recombinant Adenovirus YCI-Ad-VSVG To investigate incorporation of a nucleotide sequence encoding the VSV-G epitope into the 3' end of the fiber of the recombinant adenovirus YCI-Ad-VSVG of the present invention, PCR was carried out using the viral genome of Ad-ΔE1, YKL-1 and YCI-Ad-VSVG, prepared in B of Example 3, as template and a primer set capable of amplifying the nucleotide sequence corresponding to the VSV-G epitope: a sense primer 5'-GAA/GGG/GGA/TCC/GGC/GGG/GGC/GGT/GGA-3' (SEQ ID NO: 16); and an antisense primer: 5'-CCC/GAG/CTC/ACG/TCA/CAG/TTG/CAT/ATC-3' (SEQ ID NO: 17), where the cloning vector pSP72[805+103 bp] carrying a nucleotide sequence of 103 bp encoding the VSV-G epitope linked to a linker consisting of 8 Gly was used as a positive control.

The resulting reaction mixtures were electrophoresed on an agarose gel (FIG. 6). As apparent in FIG. 6, a PCR product of about 103 bp was not found in the PCR samples of YKL-1 and Ad-ΔE1, which harbor the native fiber gene, while being found in the PCR sample of YCI-Ad-VSVG with a nucleotide sequence encoding a VSV-G epitope incorporated into the 3' end of the fiber. Also, the 103 bp fragment was observed in the PCR sample of the positive control pSP72[805+103 bp].

EXAMPLE 4

Assay for Gene Transfer Efficiency of d1324-LacZ-VSVG

To investigate the effect of incorporation of a VSV-G epitope into the adenovirus fiber on infection efficiency, gene delivery efficiency was evaluated in a gene transfer system using the d1324-LacZ-VSVG adenovirus expressing beta-galactosidase encoded by the LacZ gene as a marker. Human brain cancer cell lines, U343, U118MG (HTB-15, ATCC, USA), U251N and U87MG (HTB-14, ATCC, USA), and other cell lines expressing CAR at low level, CHO-K1 (CCL-61, ATCC), MCF-7 (HTB-22, ATCC), Pro5 (CRL-1781, ATCC) and Lec2 (CRL-1736, ATCC), were infected with the adenovirus d1324-LacZ as a control and the d1324-LacZ-VSVG adenovirus with a VSV-G epitope attached at various multiplicities of infection (MOI), respectively. After 2 days, the infected cells were stained with X-gal (FIGS. 7a, 7b, 7c, 7e, 7f, 7g and 7h). FIGS. 7a to 7h show results of X-gal staining of the infected cell line, U343, U118MG, U251N, U87MG, CHO-K1, Lec2, MCF-7, and Pro 5, respectively. As apparent in FIGS. 7a to 7b, the expression level of LacZ gene was found to be increased in all tested cell lines, indicating that the d1324-LacZ-VSVG adenovirus had improved infection efficiency. In particular, the high expression of LacZ was found in the CHO-K1, MCF-7, Pro 5 and Lec 2 cell lines, which expressed the native receptor CAR of adenovirus at a low level and thus were not easily infected with wild-type adenovirus, indicating that the d1324-LacZ-VSVG adenovirus infected the cells in a CAR-independent manner, through binding to phosphatidyl serine highly-expressed on cell membranes of a broad range of cell types, thus remarkably increasing gene transfer efficiency to cell lines.

Increasing of the gene transfer efficiency by the incorporation of a VSV-G epitope quantitatively, and the results of X-gal staining were given as graphs (FIGS. 8a, 8b, 8c, 8d, 8e, 8f, 8g and 8h). FIGS. 8a to 8h show quantitative analysis of the results of X-gal staining of the infected cell lines, U343, U118MG, U251N, U87MG, CHO-K1, Lec2, MCF-7, and Pro 5, respectively. As shown in FIGS. 8a to 8h, expression levels of the LacZ gene greatly increased in all cell lines infected with d1324-LacZ-VSVG, indicating that the d1324-LacZ-VSVG adenovirus had increased infection efficiency. The d1324-LacZ-VSVG adenovirus showed infection efficiency increased by over 100% in U251N (MOI 1), U118MG (MOI 50), CHO-K1 (MOI 50) and Pro5 (MOI 50) cell lines, and also remarkably increased infection efficiency in other cell lines. Especially, the d1324-LacZ-VSVG adenovirus showed CAR-independent infection in the cell lines, CHO-K1, MCF-7, Pro5 and Lec2, which expressed CAR essential for infection of wild-type adenovirus at a low level, which was higher than that of the d1324-LacZ adenovirus with the fiber not modified. Also, expression levels of the LacZ gene increased with the MOI of recombinant adenovirus, indicating that the d1324LacZ-VSVG adenovirus had significantly increased transduction efficiency.

EXAMPLE 5

Assay for Tumor Cell-killing Effect of YCI-Ad-VSVG

Increased Tumor-cell killing effect of the recombinant adenovirus YCI-Ad-VSVG was investigated in carcinoma cell lines, Hep3B, Hep1, HepG2, C33A, U343, U87MG, U251-N and MCF-7. The carcinoma cell lines were infected with the replication-incompetent adenovirus dl324/LacZ, YKL-1, and YCI-Ad-VSVG at 10, 1 or 0.1 MOI, and cell viability was assessed. Their killing effect was monitored daily under a microscope. At the moment that the cells infected with any one of the virus at an MOI of 0.1 exhibited complete cell lysis, cells on the plate were then stained with 0.5% crystal violet in 50% methanol. Photographs of the stained cells are given in FIGS. 9a to 9h FIGS. 9a to 9h are photographs showing the result of cell lesion analysis for determining increased tumor-specific killing effect of YCI-Ad-VSVG on Hep3B cells, C33A cells, U343 cells, U87MG cells, Hep1 cells, U251-N cells, HepG2 cells, and MCF-7 cells, respectively, in which lane 1 shows infection with dl324/LacZ, lane 2 shows infection with YKL-1, and lane 3 shows infection with YCI-Ad-VSVG. As shown in FIGS. 9a to 9h, YCI-Ad-VSVG was found to have a tumor cell-killing effect about 100 times higher than that of YKL-1 in Hep3B and U343 cells, and about 10 times higher in other carcinoma cell lines.

These results indicated that in all tested carcinoma cell lines, the recombinant adenovirus YCI-Ad-VSVG had significantly increased oncolytic activity by the incorporation of a VSV-G epitope, in comparison with the control YKL-1.

EXAMPLE 6

MTT Assay for Tumor Cell-killing Effect of YCI-Ad-VSVG

Figure 13:
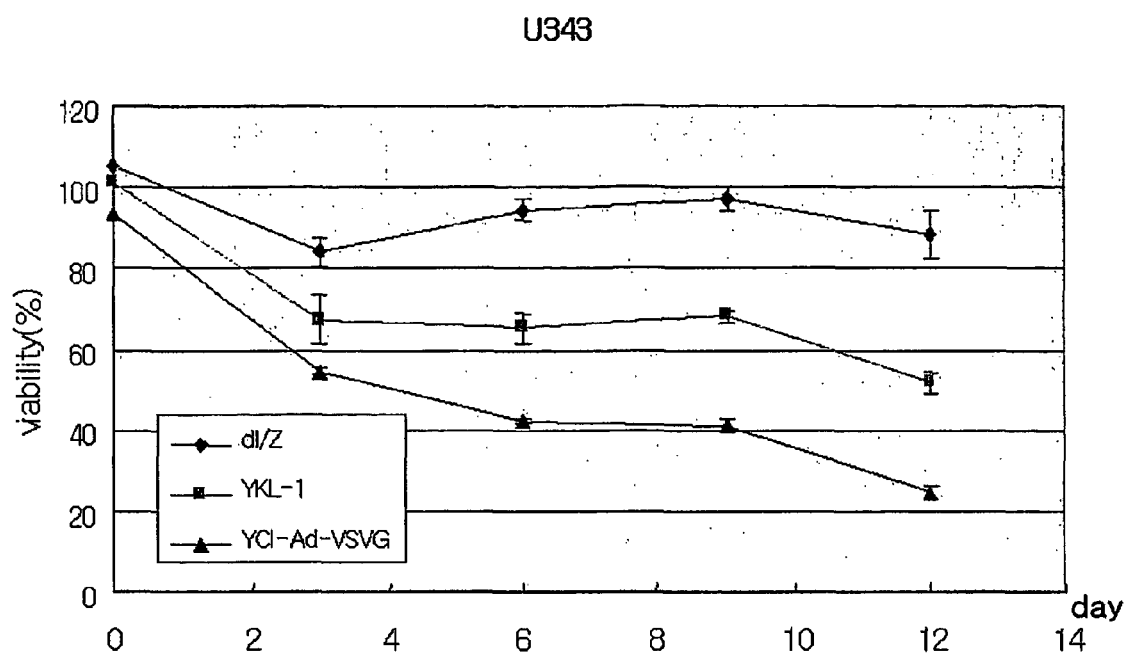
FIG. 13 is a graph showing a result of an MTT assay after infecting human brain cancer cell line U251 with 5 MOI of the recombinant adenovirus YCI-Ad-VSVG.
Figure 14:
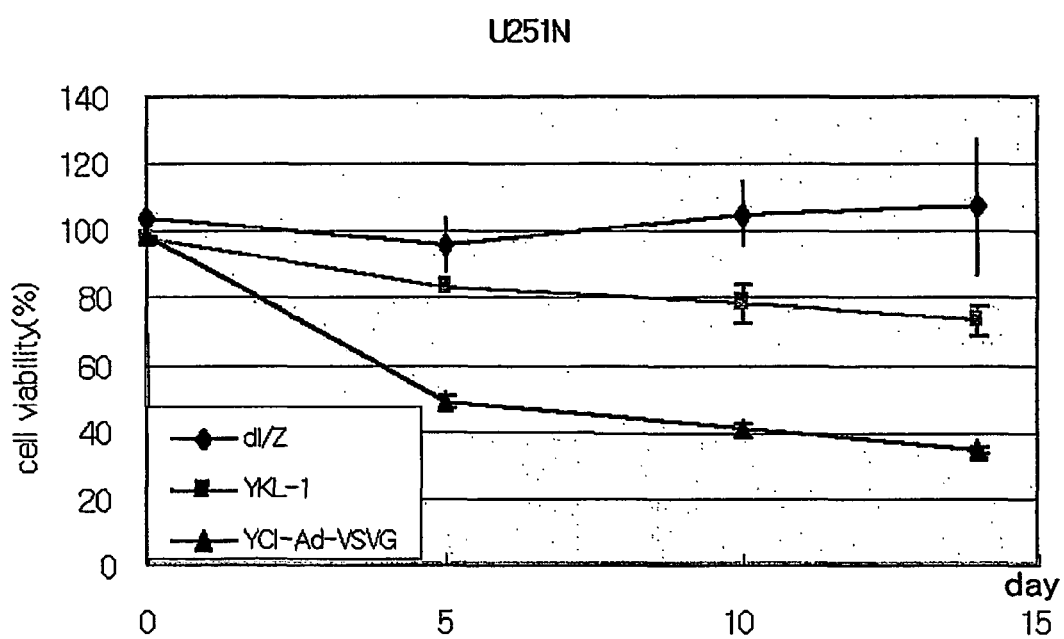
FIG. 14 is a graph showing a result of an MTT assay after infecting human brain cancer cell line U343 with 5 MOI of the recombinant adenovirus YCI-Ad-VSVG.
Figure 15:
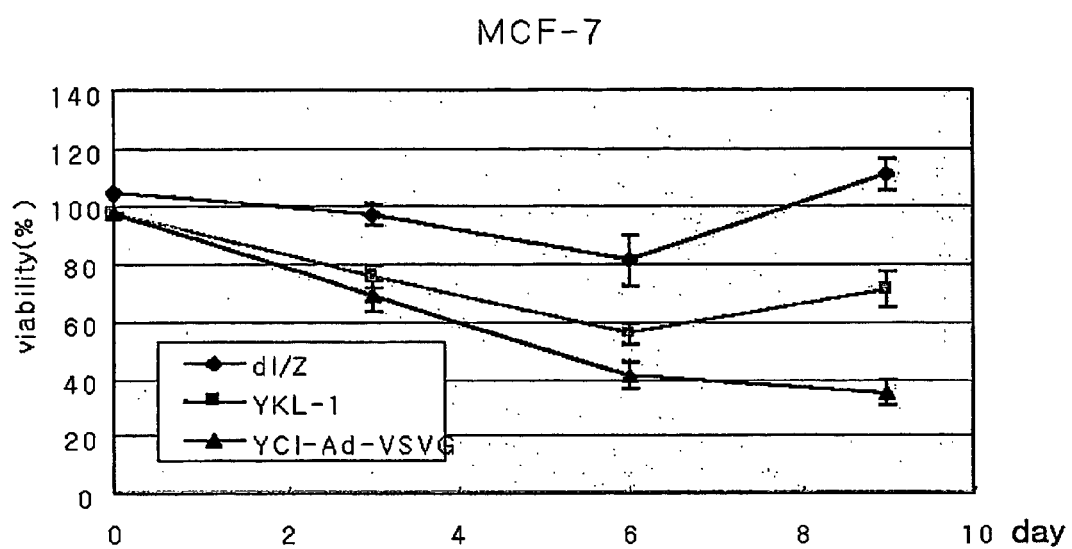
FIG. 15 is a graph showing a result of an MTT assay after infecting human ovarian cancer cell line HeLa with 10 MOI of the recombinant adenovirus YCI-Ad-VSVG.
Figure 16:
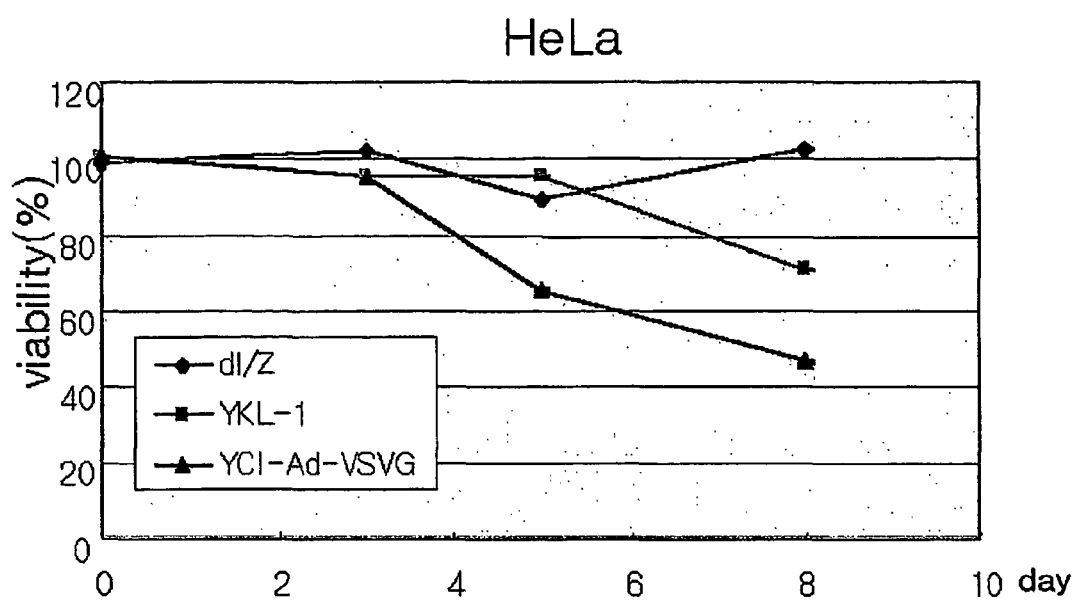
FIG. 16 is a graph showing a result of an MTT assay after infecting human breast cancer cell line MCF-7 with 100 MOI of the recombinant adenovirus YCI-Ad-VSVG.

To analyze quantitatively the tumor cell-killing effect of YCI-Ad-VSVG, after infecting various tumor cells with the replication-deficient adenovirus dl324-LacZ, the replication-competent adenovirus YKL-1, and the replication-competent adenovirus YCI-Ad-VSVG with a VSV-G epitope attached, cell viability of the infected cells was measured by MTT assay. FIGS. 13 and 14 are results of MTT assay for the human brain tumor cell lines U251 and U343, respectively, infected with an adenovirus at a multiplicity of infection (MOI) of 5, FIG. 15 is a result of MTT assay for the human ovarian cancer cell line HeLa infected with an adenovirus at 10 MOI, and FIG. 16 is a result of MTT assay for the human breast cancer cell line MCF-7 infected with an adenovirus at 100 MOI.

As apparent in FIGS. 13 to 16, when being infected with the replication-incompetent adenovirus dl324-LacZ as a negative control, no cell death was found. In contrast, when being infected with the replication-competent adenoviruses YKL-1 and YCI-Ad-VSVG, cell viability of the infected tumor cells was gradually reduced by viral proliferation increased with the passage of time. Particularly, because of having high infection efficiency due to the incorporation of a VSV-G epitope into the carboxy terminus of the fiber, the recombinant adenovirus YCI-Ad-VSVG was found to have much higher oncolytic activity than YKL-1.

EXAMPLE 7

Testing of Antitumor Effect of YCI-Ad-VSVG in a Nude Mouse Model

In vivo assay for measuring antitumor effect of the recombinant adenovirus YCI-Ad-VSVG was performed using nude mice. Human hepatoma cell line Hep3B (1B-8044, ATCC, USA), human brain cancer cell line U343, or human brain cancer cell line U87MG (HTB-14, ATCC, USA) was subcutaneously injected to nude mice 5-6 weeks old (Charles River Japan Inc., Japan). When tumor size reached 5×5 mm, the recombinant adenovirus YCI-Ad-VSVG at a concentration of 5×10$^8$ pfu/50 µl, which dialyzed with PBS after being recovered by ultracentrifugation, was injected to the tumors. The size of tumor was measured using calipers once every 2-3 days, and the results are given in FIGS. 17 to 19.

Figure 17:
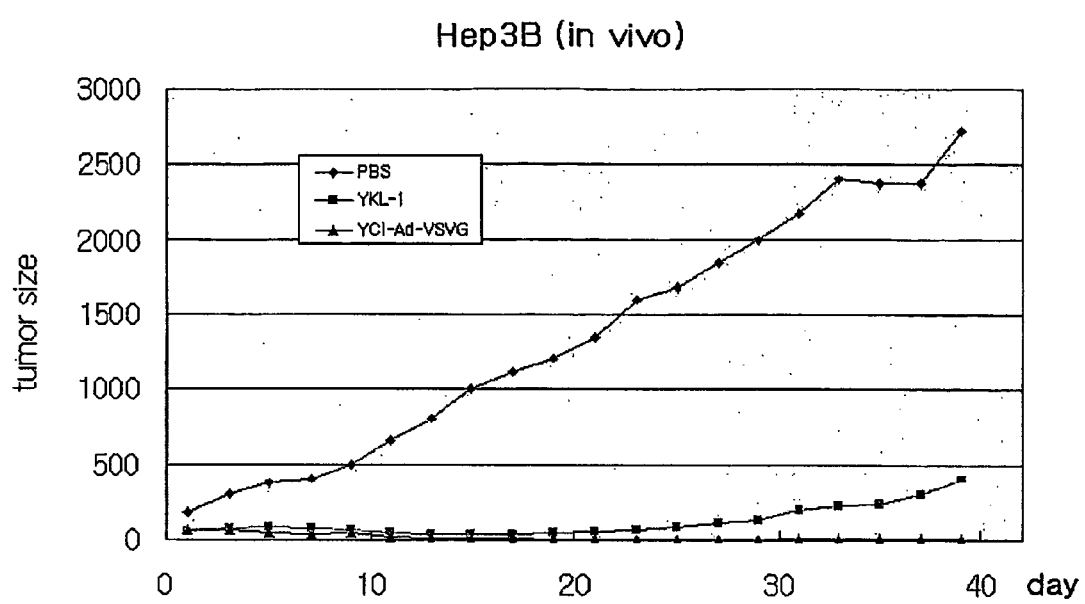
FIG. 17 is a graph showing inhibitory effect of the recombinant adenovirus YCI-Ad-VSVG on the growth of Hep3B tumor cells produced in nude mouse.
Figure 18:
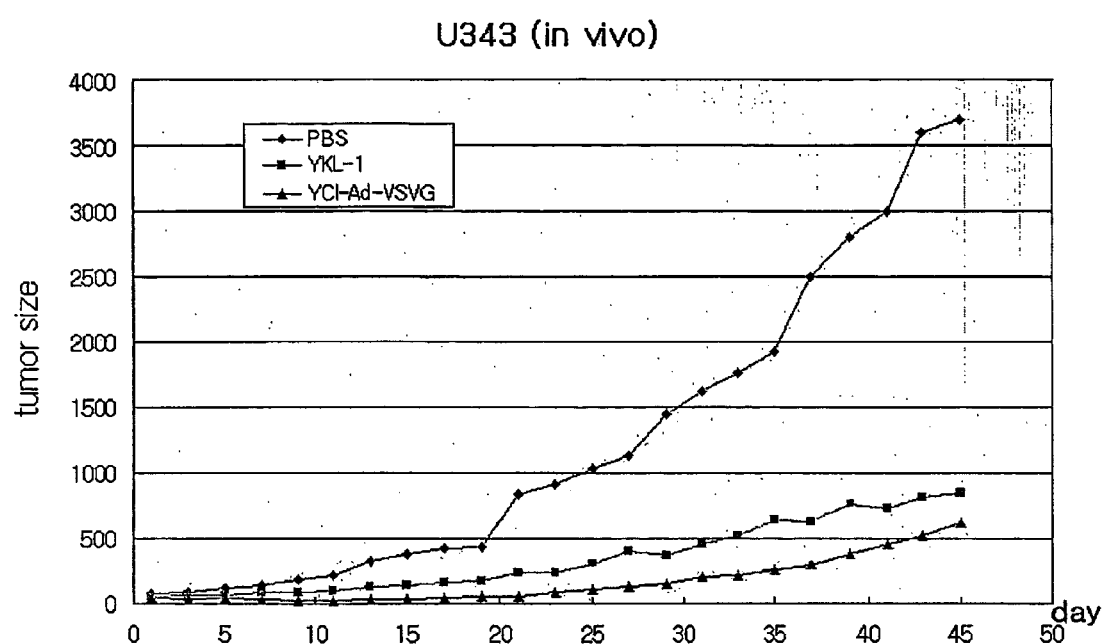
FIG. 18 is a graph showing inhibitory effect of the recombinant adenovirus YCI-Ad-VSVG on the growth of U343 tumor cells produced in nude mouse.
Figure 19:
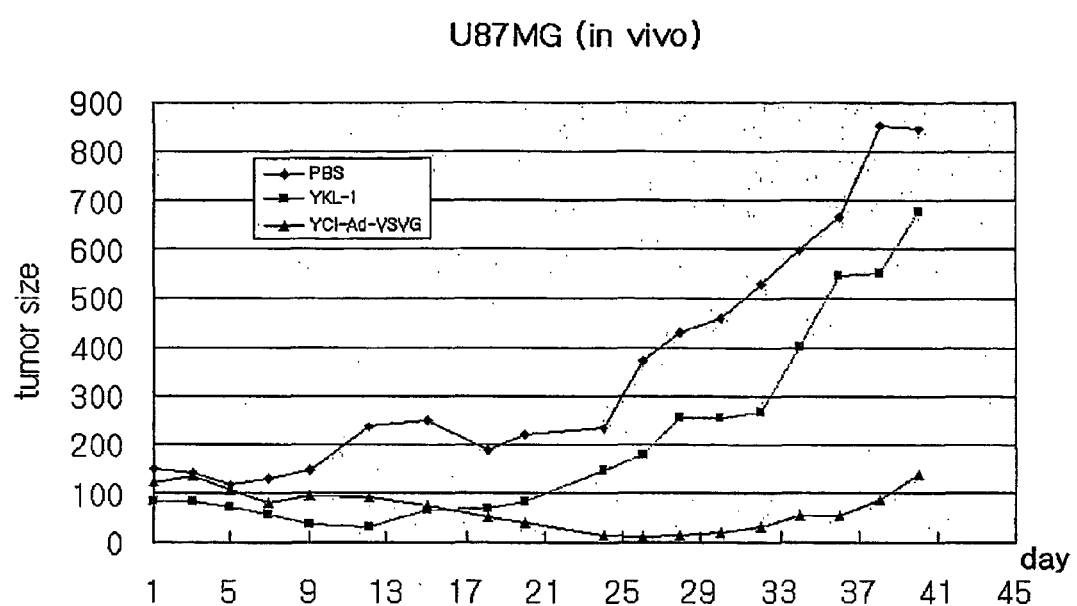
FIG. 19 is a graph showing inhibitory effect of the recombinant adenovirus YCI-Ad-VSVG on the growth of U87MG cells produced in nude mouse.

As shown in FIGS. 17 to 19, in a control group receiving only PBS, tumor size was increased with the passage of time. In contrast, in mice injected with the YCI-Ad-VSVG adenovirus, tumor growth was significantly inhibited. In addition, inhibition of tumor growth was also seen in mice infected with the YKL-1 adenovirus, but antitumor efficacy of YKL-1 was lower than that of YCI-Ad-VSVG.

These results indicate that the recombinant adenovirus YCI-Ad-VSVG of the present invention had excellent antitumor effect in vivo. Such high antitumor efficacy of YCI-Ad-VSVG is attributed to CAR-independent infection via the VSV-G epitope incorporated into the carboxy terminus of the fiber, thus enabling the YCI-Ad-VSVG adenovirus to enter tumor cells with low CAR expression at high efficiency.

EXAMPLE 8

Assay for Viral Titer of YCI-Ad-VSVG 293 cells were infected with 10 MOI of each of the replication-incompetent adenovirus dl324-LacZ and the adenovirus dl324-LacZ-VSVG with a VSV-G epitope attached. 24, 48 and 72 hrs after infection, cell pellets and supernatants were collected, and viral titer was then measured. The results are given in Table 1, below, and FIG. 20.

TABLE 1

| Incubation time after infection | Viral titer of dl324/LacZ | Viral titer of dl324/LacZ/VSVG |
|---|---|---|
| 24 | 16,000,000 | 20,000,000 |
| 48 | 200,000,000 | 399,000,000 |
| 72 | 320,000,000 | 502,000,000 |

Figure 20:
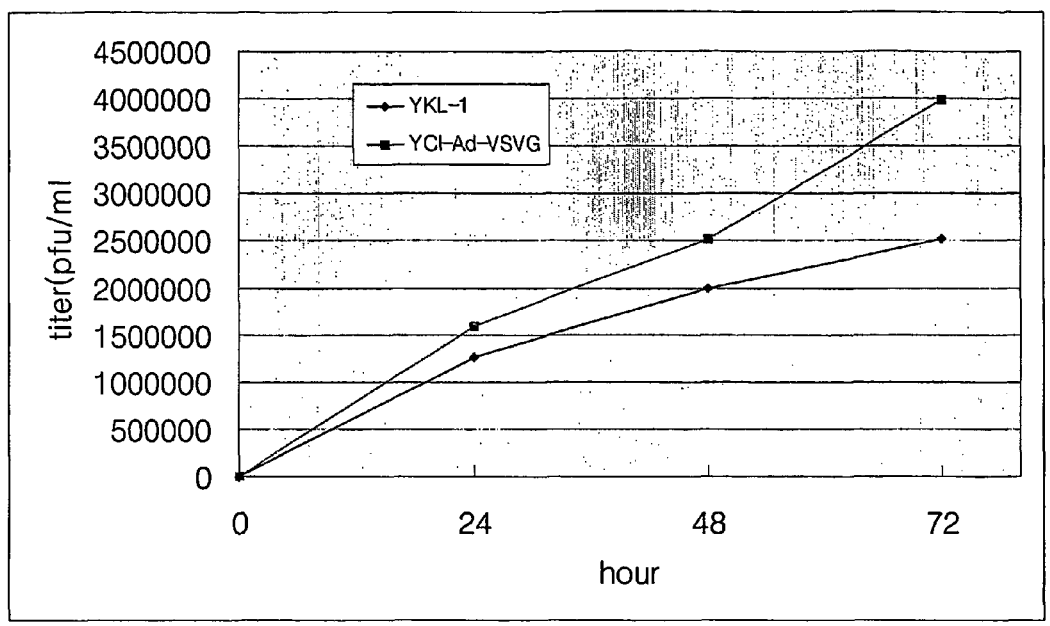
FIG. 20 is a graph showing viral titer of the recombinant adenovirus dl324-LacZ-VSVG after infecting 293 cells with 10 MOI of the recombinant adenovirus.

As apparent in Table 1 and FIG. 20, the dl324-LacZ-VSVG adenovirus produced viral particles in high titer due to its increased infection efficiency.

In addition, to investigate the increased viral titer of YCI-Ad-VSVG, brain cancer cell line U251N was infected with 10 MOI of each of the replication-competent adenoviruses YKL-1 and YCI-Ad-VSVG. 24 hr, 48 hr and 72 hr after infection, cell pellets and supernatants were collected, and viral titer was then measured. The results are given in Table 2, below, and FIG. 21.

TABLE 2

| Incubation time after infection | Viral titer of YKL-1 | Viral titer of YCI-Ad-VSVG |
|---|---|---|
| 24 | 12,600,000 | 15,900,000 |
| 48 | 20,000,000 | 25,200,000 |
| 72 | 25,200,000 | 39,900,000 |

Figure 21:
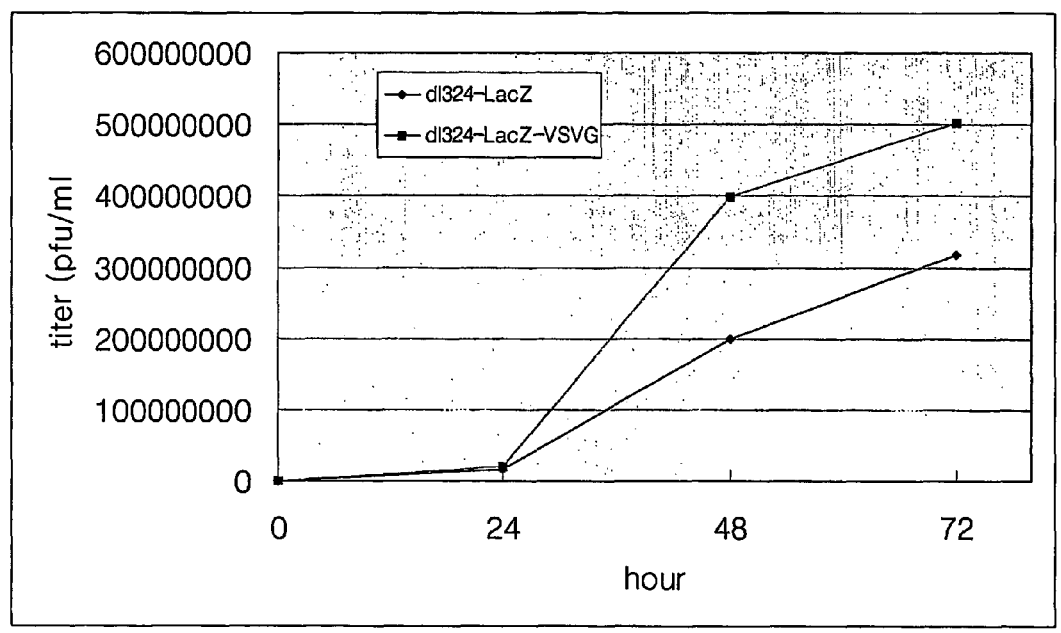
FIG. 21 is a graph showing viral titer of the recombinant adenovirus YCI-Ad-VSVG after infecting human brain cancer cell line U251N with 10 MOI of the recombinant adenovirus.

As apparent in Table 2 and FIG. 21, the YCI-Ad-VSVG adenovirus with a VSV-G epitope incorporated into the carboxy terminus of the fiber showed higher virus yeilds than the YKL-1 adenovirus with a native fiber protein.

INDUSTRIAL APPLICABILITY

As described hereinbefore, the present invention provides a recombinant adenovirus prepared by introducing a part of a ligand responsible vesicular stomatitis virus (VSV) entry into adenovirus, which has improved therapeutic efficiency, and a pharmaceutical composition comprising such a recombinant adenovirus.

In accordance with the present invention, through the incorporation of a VSV-G epitope into the carboxy terminus of the fiber, the recombinant adenovirus according to the present invention has increased infection efficiency, especially for cells not infected easily with wild-type adenovirus, thus enhancing its transduction efficiency and generation of viral particles in the infected cells. In addition, such high infection efficiency allows the recombinant adenovirus to be administered at a lower amount, thereby minimizing the host humoral and cellular immune response to viral proteins and viral infected cells, as well as the combination therapy with radiotherapy or chemotherapy, thus being useful for development of new gene therapies capable of maximizing therapeutic effect.

What is claimed is:

1. A recombinant adenovirus wherein the construct is YCI-Ad-VSVG, wherein the recombinant adenovirus is capable of targeting and productively infecting a cancer cell.

2. A pharmaceutical composition comprising: (a) a recombinant adenovirus of claim 1, and (b) a pharmaceutically acceptable carrier.

3. A recombinant plasmid expressing the recombinant adenovirus of claim 1.

4. A host cell transformed or transfected with the recombinant plasmid of claim 3.

* * * * *

SEQUENCE LISTING

<160> NUMBER OF SEQ ID NOS: 17

<210> SEQ ID NO 1
<211> LENGTH: 29
<212> TYPE: DNA
<213> ORGANISM: Artificial Sequence
<220> FEATURE:
<223> OTHER INFORMATION: primer

<400> SEQUENCE: 1
ttattggatc ctttgtctag ggccgcggg 29

<210> SEQ ID NO 2
<211> LENGTH: 40
<212> TYPE: DNA
<213> ORGANISM: Artificial Sequence
<220> FEATURE:
<223> OTHER INFORMATION: primer

<400> SEQUENCE: 2
tcttggatcc agatctatac agttaagcca cctatacaac 40

<210> SEQ ID NO 3
<211> LENGTH: 29
<212> TYPE: DNA
<213> ORGANISM: Artificial Sequence
<220> FEATURE:
<223> OTHER INFORMATION: primer

<400> SEQUENCE: 3
ttattggatc ctttgtctag ggccgcggg 29

<210> SEQ ID NO 4
<211> LENGTH: 35
<212> TYPE: DNA
<213> ORGANISM: Artificial Sequence
<220> FEATURE:
<223> OTHER INFORMATION: primer

<400> SEQUENCE: 4
ccaggatcca gatctcccca tttaacacgc catgc 35

<210> SEQ ID NO 5
<211> LENGTH: 40
<212> TYPE: DNA
<213> ORGANISM: Artificial Sequence
<220> FEATURE:
<223> OTHER INFORMATION: primer

<400> SEQUENCE: 5
gttacatctg acctcctgta ggctagcgag tgtttggaag 40

<210> SEQ ID NO 6
<211> LENGTH: 40
<212> TYPE: DNA
<213> ORGANISM: Artificial Sequence
<220> FEATURE:
<223> OTHER INFORMATION: primer

<400> SEQUENCE: 6
cttccaaaca ctcgctagcc tacaggaggt cagatgtaac          40

<210> SEQ ID NO 7
<211> LENGTH: 20
<212> TYPE: DNA
<213> ORGANISM: Artificial Sequence
<220> FEATURE:
<223> OTHER INFORMATION: primer

<400> SEQUENCE: 7
ggcctttact tgtttacagc                                20

<210> SEQ ID NO 8
<211> LENGTH: 35
<212> TYPE: DNA
<213> ORGANISM: Artificial Sequence
<220> FEATURE:
<223> OTHER INFORMATION: primer

<400> SEQUENCE: 8
ggggagctcg gatcctcctt cttgggcaat gtatg               35

<210> SEQ ID NO 9
<211> LENGTH: 19
<212> TYPE: PRT
<213> ORGANISM: Vesicular stomatitis virus

<400> SEQUENCE: 9

Gly Thr Trp Leu Asn Pro Gly Phe Pro Pro Gln Ser Cys Gly Tyr Ala
 1               5                  10                  15

Thr Val Thr

<210> SEQ ID NO 10
<211> LENGTH: 57
<212> TYPE: DNA
<213> ORGANISM: Vesicular stomatitis virus

<400> SEQUENCE: 10
ggaacttggc tgaatccagg cttccctcct caaagttgtg gatatgcaac tgtgacg     57

<210> SEQ ID NO 11
<211> LENGTH: 92
<212> TYPE: DNA
<213> ORGANISM: Artificial Sequence
<220> FEATURE:
<223> OTHER INFORMATION: oligomer

<400> SEQUENCE: 11
gatccggcgg gggcggtgga ggaggggtg gaacttggct gaatccaggc ttccctcctc   60
aaagttgtgg atatgcaact gtgacgtgag ct                                92

<210> SEQ ID NO 12
<211> LENGTH: 27
<212> TYPE: DNA
<213> ORGANISM: Artificial Sequence
<220> FEATURE:
<223> OTHER INFORMATION: primer

<400> SEQUENCE: 12 gaaggggat ccggcggggg cggtgga                         27

```
<210> SEQ ID NO 13
<211> LENGTH: 27
<212> TYPE: DNA
<213> ORGANISM: Artificial Sequence
<220> FEATURE:
<223> OTHER INFORMATION: primer

<400> SEQUENCE: 13
cccgagctca cgtcacagtt gcatatc                                              27

<210> SEQ ID NO 14
<211> LENGTH: 21
<212> TYPE: DNA
<213> ORGANISM: Artificial Sequence
<220> FEATURE:
<223> OTHER INFORMATION: primer

<400> SEQUENCE: 14
tttgtgttac tcatagcgcg t                                                    21

<210> SEQ ID NO 15
<211> LENGTH: 21
<212> TYPE: DNA
<213> ORGANISM: Artificial Sequence
<220> FEATURE:
<223> OTHER INFORMATION: primer

<400> SEQUENCE: 15
attctttccc acccttaagc c                                                    21

<210> SEQ ID NO 16
<211> LENGTH: 27
<212> TYPE: DNA
<213> ORGANISM: Artificial Sequence
<220> FEATURE:
<223> OTHER INFORMATION: primer

<400> SEQUENCE: 16 gaaggggat ccggcggggg cggtgga                                               27

<210> SEQ ID NO 17
<211> LENGTH: 27
<212> TYPE: DNA
<213> ORGANISM: Artificial Sequence
<220> FEATURE:
<223> OTHER INFORMATION: primer

<400> SEQUENCE: 17
cccgagctca cgtcacagtt gcatatc                                              27
```